(12) United States Patent
Winkler et al.

(10) Patent No.: US 8,791,298 B2
(45) Date of Patent: Jul. 29, 2014

(54) USE OF METAL HYDRAZIDE COMPLEX COMPOUNDS AS OXIDATION CATALYSTS

(71) Applicant: BASF SE, Ludwigshafen (DE)

(72) Inventors: Barbara Winkler, Lorrach (DE); Hauke Rohwer, Lorrach (DE); Marie-Josee Dubs, Wittersdorf (FR); Menno Hazenkamp, Riehen (CH); Kai Eichin, Kandern (DE); Albert Schneider, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/920,381

(22) Filed: Jun. 18, 2013

(65) Prior Publication Data
US 2013/0281353 A1    Oct. 24, 2013

Related U.S. Application Data

(62) Division of application No. 12/936,699, filed as application No. PCT/EP2009/053722 on Mar. 30, 2009, now Pat. No. 8,492,324.

(30) Foreign Application Priority Data

Apr. 9, 2008 (EP) .................... 08154246

(51) Int. Cl.
*C07C 251/00* (2006.01)
*C07C 251/28* (2006.01)
*C07C 251/02* (2006.01)
*C11D 3/28* (2006.01)
*C11D 3/32* (2006.01)
*C11D 7/32* (2006.01)
*B01J 27/20* (2006.01)
*B01J 27/24* (2006.01)
*A01N 47/34* (2006.01)

(52) U.S. Cl.
CPC .. *C11D 3/28* (2013.01); *C11D 3/32* (2013.01); *C11D 3/323* (2013.01); *C11D 7/3209* (2013.01); *C11D 7/3263* (2013.01); *C11D 7/3281* (2013.01); *A01N 47/34* (2013.01); *B01J 27/20* (2013.01); *B01J 27/24* (2013.01)

USPC .............. 564/36; 564/37; 510/376; 510/499; 510/500; 510/501; 502/200; 502/324; 502/325

(58) Field of Classification Search
CPC .............. C11D 1/54; C11D 3/28; C11D 3/32; C11D 3/323; C11D 7/3209; C11D 7/3263; C11D 7/3281; A01N 47/34; B01J 27/20; B01J 27/24
USPC ......... 510/202, 303, 311, 372, 376, 499, 500, 510/501; 502/200, 324, 325; 564/36, 37
See application file for complete search history.

(56) References Cited

U.S. PATENT DOCUMENTS

| | | |
|---|---|---|
| 2,670,348 A | 2/1954 | Gregory |
| 4,436,736 A | 3/1984 | Hodakowski |

FOREIGN PATENT DOCUMENTS

DE    196 39 603 A1    4/1998

OTHER PUBLICATIONS

English Language Abstract of DE 19639603 printed on Jan. 13, 2011.
Gasparini et al., Chemical Communications, Jan. 19, 2007 (13), pp. 1340-1342.
Leovac et al. Journal of Thermal Analysis and Calorimetry (2006) vol. 86 (2), pp. 379-384.
Shallaby et al., Journal of Inorganic and Nuclear Chemistry (1979) vol. 41 (2) pp. 267-269.
Mohan et al., Inorganic Chemica Acta, vol. 152, No. 1, Jan. 1, 1988, pp. 25-36.
Pouralimardan et al., Inorganic Chemica Acta, vol. 360, No. 5, Mar. 8, 2007, pp. 1599-1608.
European Search report dated Sep. 9, 2008.
Machine Translation of claims of DE 19639603, Aug. 2012.
Machine Translation of specification of DE 19639603, Aug. 2012.

*Primary Examiner* — Gregory R Delcotto
(74) *Attorney, Agent, or Firm* — Shiela A. Loggins

(57) ABSTRACT

The present invention relates to the use of selected metal complex compounds and ligands as oxidation catalysts as well as to a process for removing stains and soil on textiles and hard surfaces. The metal complex compounds have hydrazide ligands, preferably with electron withdrawing groups in the phenyl ring adjacent to the acyl group. Further aspects of the invention are formulations comprising such metal complex compounds, novel metal complex compounds and novel ligands.

1 Claim, No Drawings

USE OF METAL HYDRAZIDE COMPLEX COMPOUNDS AS OXIDATION CATALYSTS

This application is a divisional of U.S. application Ser. No. 12/936,699, filed Dec. 1, 2010, granted which is a national stage of PCT/EP 2009/053722, filed Mar. 30, 2009, the contents of both herein incorporated entirely by reference.

The present invention relates to the use of selected metal complex compounds as oxidation catalysts as well as to a process for removing stains and soil on textiles and hard surfaces. The metal complex compounds have hydrazide ligands, preferably with electron withdrawing groups or moieties adjacent to the acyl group. Further aspects of the invention are formulations comprising such metal complex compounds, novel metal complex compounds and novel ligands.

Metal complex catalysts with hydrazide ligands have in generally been described as oxidation catalysts, for example, in DE 196 39 603. However, the compounds disclosed are not active enough. The instant invention solves this problem by introducing electron withdrawing groups in the phenyl ring adjacent to the acyl group.

The instant metal complex compounds are used especially for enhancing the action of peroxides, for example in the treatment of textile material, without at the same time causing any appreciable damage to fibres and dyeings. There is also no appreciable damage to fibres and dyeings if these metal complexes are used in combination with an enzyme or a mixture of enzymes.

The instant metal complex compounds may also be used as catalysts for oxidation using molecular oxygen and/or air, that is, without peroxide compounds and/or peroxide-forming substances. The bleaching of the fabric can happen during and/or after the treatment of the fibre with the formulation, which comprises the metal complexes.

Peroxide-containing bleaching agents have long been used in washing and cleaning processes. They have an excellent action at a liquor temperature of 90° C. and above, but their performance noticeably decreases with lower temperatures. Various transition metal ions added in the form of suitable salts, and coordination compounds containing such cations are known to activate $H_2O_2$. In that manner it is possible for the bleaching effect, which is unsatisfactory at lower temperatures, of $H_2O_2$ or precursors that release $H_2O_2$ and of other peroxo compounds, to be increased. They are important for practical purposes, in that respect, especially combinations of transition metal ions and ligands of which the peroxide activation is manifested in an increased tendency towards oxidation in relation to substrates and not only in a catalase-like disproportionation. The latter activation, which in the present case tends rather to be undesirable, could even impair the bleaching effects, which are inadequate at low temperatures, of $H_2O_2$ and its derivatives.

In terms of $H_2O_2$ activation having effective bleaching action, mononuclear and polynuclear variants of manganese complexes having various ligands, especially 1,4,7-trimethyl-1,4,7-triazacyclononane and optionally oxygen-containing bridging ligands, are currently regarded as being especially effective. Such catalysts are adequately stable under practical conditions and, with $Mn^{m+}$, contain an ecologically acceptable metal cation, but their use is unfortunately associated with considerable damage to dyes and fibres.

The aim of the present invention is accordingly to provide improved metal complex catalysts for oxidation processes that meet the above requirements and, especially, enhance the action of peroxide compounds in the most varied fields of application without causing any appreciable damage.

One aspect of the invention is the use, as a catalyst for oxidation reactions, of at least one complex of formula (1)

wherein
Me is manganese, titanium, iron, cobalt, nickel or copper;
X is a coordinating or bridging radical;
n is an integer from 1 to 4;
m is an integer from 0 to 2;
p is an integer having a value of from 0 to 10;
z is the charge of the metal complex,
Y is a counter-ion,
q=z/(charge of Y), and
L is a ligand of formula (2)

wherein
$R_1$ denotes $CF_3$ or $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl which are substituted by one or more electron withdrawing substituents; or
phenyl or naphthyl which are substituted by one or more electron withdrawing substituents;
$R_4$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl;
$R_2$ and $R_3$ independently of each other denote hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl or unsubstituted or substituted heteroaryl; or
$R_2$ and $R_3$, together with the alkylidene carbon atom linking them, form an unsubstituted or substituted 5-, 6-, 7-, 8- or 9-membered ring which may contain further hetero atoms.

Under electron withdrawing substituents there are understood such substituents which have a −I and/or −M effect in aromatic ring systems.

Me represents a metal selected from manganese, titanium, iron, cobalt, nickel or copper, preferably from Mn(II)-(III)-(IV)-(V), Cu(I)-(II)-(III), Fe(I)-(II)-(III)-(IV), Co(I)-(II)-(III), Ni(I)-(II)-(III), Ti(II)-(III)-(IV) and more preferably selected from Mn(II)-(III)-(IV)-(V), Cu(I)-(II)-(III), Fe(I)-(II)-(III)-(IV) and Co(I)-(II)-(III).

L represents a ligand as herein defined, or its protonated or deprotonated analogue.

Where applicable the acyl hydrazone derivatives can be in their E- or Z-configuration. When $R_4$ is hydrogen the ligand of formula (2) may be in one of its tautomeric forms or as a mixture of its different tautomeric forms.

Suitable substituents for the alkyl, heteroalkyl, cycloalkyl, alkenyl, cycloalkenyl, alkinyl, phenyl, naphthyl, aralkyl, heteroaralkyl and cycloheteroalkyl groups are especially $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy; preferably hydroxyl, halogen and $C_1$-$C_4$alkoxy.

In general unsubstituted alkyl, heteroalkyl, cycloalkyl, alkenyl, cycloalkenyl, alkinyl, phenyl, naphthyl, aralkyl, heteroaralkyl and cycloheteroalkyl are preferred.

Cyclic compounds are preferably 5-, 6- or 7-membered rings, 6-membered rings are preferred.

Aryl is phenyl or naphthyl.

The $C_1$-$C_{18}$alkyl radicals mentioned for the compounds of formula (2) are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formula (2) are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1$-$C_4$alkyl, $C_1$-$C_4$alkoxy, phenyl and hydroxy.

Special preference is given to the corresponding phenyl radicals.

The $C_1$-$C_6$alkylene groups mentioned for the compounds of formula (2) are, for example, straight-chain or branched alkylene radicals, such as methylene, ethylene, n-propylene or n-butylene. $C_1$-$C_4$alkylene groups are preferred. The alkylene radicals mentioned may be unsubstituted or substituted, for example by hydroxy or $C_1$-$C_4$alkoxy.

In the compounds of formulae (1) and (2), halogen is preferably chlorine, bromine or fluorine, with special preference being given to chlorine.

$C_3$-$C_{12}$cycloalkyl refers to saturated cyclic hydrocarbons. $C_3$-$C_{12}$Cycloalkyl is for example cyclopropyl, cyclobutyl, cyclopentyl, cyclohexyl, trimethylcyclohexyl, menthyl, thujyl, bornyl, 1-adamantyl oder 2-adamantyl.

$C_2$-$C_{18}$alkenyl is for example vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or signifies different isomers of hexenyl, octenyl, nonenyl, decenyl or dodecenyl.

$C_3$-$C_{12}$ cycloalkenyl refers to unsaturated hydrocarbon residues containing one or multiple double bonds such, 2-cyclobuten-1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl or 7,7-dimethyl-2,4-norcaradien-3-yl.

$C_7$-$C_9$ aralkyl is for example benzyl, β-phenyl-ethyl, α,α-dimethylbenzyl.

$C_5$-$C_{16}$heteroaralkyl signifies for example a $C_1$-$C_8$ alkyl moiety which is substituted with a $C_4$-$C_8$heteroaryl group, preferably with a $C_5$-$C_6$heteroaryl group.

$C_5$-$C_6$heteroaryl is for example pyridine or pyrimidine.

X represents any coordinating or bridging species, preferably selected from any mono-, bi- or tri-charged anions and any neutral molecules able to coordinate the metal in a mono-, bi- or tri-dentate manner, preferably selected from $O_2^{2-}$, $O^{2-}$, $RBO_2^{2-}$, $RCOO^-$, $RCONR^-$, $HOO^-$, $OH^-$, $RO^-$, $NO_3^-$, $NO_2^-$, $NO$, $CO$, $S^{2-}$, $RS^-$, $PO_4^{4-}$, STP-derived anions, $PO_3OR^{3-}$, $H_2O$, $CO_3^{2-}$, $HCO_3^-$, $ROH$, $NRR'R''$, $CH_3CN$, $RCN$, $Cl^-$, $Br^-$, $OCN^-$, $SCN^-$, $CN^-$, $N_3^-$, $F^-$, $I^-$, $RO^-$, $ClO_4^-$, $SO_4^{2-}$, $HSO_4^-$, $SO_3^{2-}$, $RSO_3^-$, $LMeO^-$ and $LMeOO^-$, and more preferably selected from $O_2^{2-}$, $O_2^{2-}$, $RBO_2^{2-}$, $RCOO^-$ (preferably $CH_3COO^-$), $HOO^-$, $OH^-$, $RO^-$, $NO_3^-$, $NO_2^-$, $NO$, $CO$, $S^{2-}$, $RS^-$, $PO_4^{4-}$, $PO_3OR^{3-}$, $H_2O$, $CO_3^{2-}$, $HCO_3^-$, $ROH$, $NRR'R''$, $CH_3CN$, $RCN$, $Cl^-$, $Br^-$, $OCN^-$, $SCN^-$, $CN^-$, $N_3^-$, $F^-$, $I^-$, $RO^-$, $ClO_4^-$, $SO_4^{2-}$, $HSO_4^-$, $SO_3^{2-}$, $RSO_3^-$ (preferably $CF_3SO_3^-$), wherein R is as defined below, L and Me have the definitions and preferred meanings given herein above and herein below. R is especially preferably hydrogen, $C_1$-$C_4$alkyl or phenyl, especially hydrogen.

Y represents any non-coordinated counter ion, preferably selected from $RCOO^-$, $ClO_4^-$, $BF_4^-$, $PF_6^-$, $RSO_3^-$, $RSO_4^-$, $SO_4^{2-}$, $S_2O_6^-$, $OCN^-$, $SCN^-$, $NO_3^-$, $NO_2^-$, $F^-$, $Cl^-$, $Br^-$, $I^-$, $RO^-$, $ClO_4^-$, $BR_4^-$, $FeCl_4^-$, $RBO_2^-$, $SO_3^{2-}$, $HSO_4^{2-}$, $N^+RR'R''R'''$, $SbCl_6^-$, $CuCl_4^-$, $CN^-$, $PO_4^{3-}$, $HPO_4^{2-}$, $H_2PO_4^{2-}$, STP-derived anions, $CO_3^{2-}$, $HCO_3^-$, $Li^+$, $Ba^{2+}$, $Na^+$, $Mg^{2+}$, $K^+$, $Ca^{2+}$, $Cs^+$ and $PR_4^+$ and more preferably selected from $RCOO^-$, $ClO_4^-$, $BF_4^-$, $PF_6^-$, $RSO_3^-$, $RSO_4^-$ (preferably $CF_3SO_3^-$), $SO_4^{2-}$, $S_2O_6^-$, $OCN^-$, $SCN^-$, $NO_3^-$, $NO_2^-$, $F^-$, $Cl^-$, $Br^-$, $I^-$, $RO^-$, $ClO_4^-$, $BR_4^-$, $FeCl_4^-$, $RBO_2^-$, $SO_3^{2-}$, $HSO_4^{2-}$, $N^+RR'R''R'''$, $SbCl_6^-$, $CuCl_4^-$, $PO_4^{3-}$, $HPO_4^{2-}$, $H_2PO_4^{2-}$, $CO_3^{2-}$, $HCO_3^-$, $Li^+$, $Ba^{2+}$, $Na^+$, $Mg^{2+}$, $K^+$, $Ca^{2+}$ and $Cs^+$.

R R', R'', R''' independently represent a group selected from hydrogen, hydroxyl, —$OR_{10}$ wherein $R_{10}$ is alkyl, alkenyl, cycloalkyl, heterocycloalkyl, aryl, heteroaryl or a carbonyl derivative group. Preferably R, R', R'', R''' represent hydrogen, optionally substituted alkyl or optionally substituted aryl, more preferably hydrogen or optionally substituted phenyl, naphthyl or $C_{1-4}$-alkyl;

Y can also be a customary organic counter-ion, for example citrate, oxalate or tartrate.

The counter ions Y in formula (1) balance the charge z on the complex formed by the ligand L, metal Me and coordinating or bridging species X. Thus, if the charge z is positive, Y may be an anion such as $RCOO^-$, $ClO_4^-$, $BF_4^-$, $PF_6^-$, $RSO_3^-$, $RSO_4^-$ (preferably $CF_3SO_3^-$), $SO_4^{2-}$, $OCN^-$, $SCN^-$, $NO_3^-$, $F^-$, $Cl^-$, $Br^-$, $I^-$, $RO^-$, $ClO_4^-$, $HSO_4^{2-}$, $PO_4^{3-}$, $HPO_4^{2-}$, $H_2PO_4^{2-}$, $CO_3^{2-}$ or $HCO_3^-$, with R being hydrogen, optionally substituted alkyl or optionally substituted aryl. If z is negative, Y may be a common cation such as an alkali metal, alkaline earth metal or (alkyl)ammonium cation.

The charge of the counter-ion Y is accordingly preferably 1+, 2+, 1− or 2−, especially 1+ or 1−. Particularly 1−.

For the compounds of formula (1), n is preferably an integer having a value of from 1 to 4, preferably 1 or 2 and especially 1.

For the compounds of formula (1), m is preferably an integer having a value of 1 or 2, especially 1.

For the compounds of formula (1), p is preferably an integer having a value of from 0 to 4, especially 2.

For the compounds of formula (1), z is preferably an integer having a value of from 8− to 8+, especially from 4− to 4+ and especially preferably from 0 to 4+. z is more especially the number 0.

For the compounds of formula (1), q is preferably an integer from 0 to 8, especially from 0 to 4, and is especially preferably the number 0.

Preferably X is $CH_3CN$, $H_2O$, $F^-$, $Cl^-$, $Br^-$, $HOO^-$, $O_2^{2-}$, $O^{2-}$, $R_{28}COO^-$, $R_{28}O^-$, $LMeO^-$ and $LMeOO^-$; Y is $R_{28}COO^-$, $ClO_4^-$, $BF_4^-$, $PF_6^-$, $R_{28}SO_3^-$, $R_{28}SO_4^-$, $SO_4^{2-}$, $NO_3^-$, $F^-$, $Cl^-$, $Br^-$ and $I^-$;

$R_{28}$ is hydrogen, unsubstituted or substituted $C_1$-$C_{18}$alkyl or phenyl.

Preferably $R_1$ is —$(CH_2)_k$—$N^+(R_{100}R'_{100}R''_{100})_3 A^-$, wherein $A^-$ is an anion and k is a number from 1 to 4; or phenyl substituted with 1 to 5 electron withdrawing substituents selected from the group consisting of
—O—C(O)OR$_{100}$, —COOR$_{100}$, —C(O)N(R$_{100}$R'$_{100}$), —C(O)—R$_{100}$, —CN, —NO$_2$, —SO$_3$R$_{100}$, —CF$_3$, F, Cl, Br, I, —N(R$_{100}$R'$_{100}$R''$_{100}$)$_3^+$A$^-$, —N(R$_{101}$R'$_{101}$) and

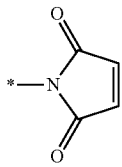

wherein $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; * is the point of attachment and $A^-$ is an anion, $R_{101}$, $R'_{101}$ independently are —C(O)—R$_{100}$, —C(O)N(R$_{100}$R'$_{100}$) or —C(O)OR$_{100}$;

or $R_1$ together with the electron withdrawing substituent is a group

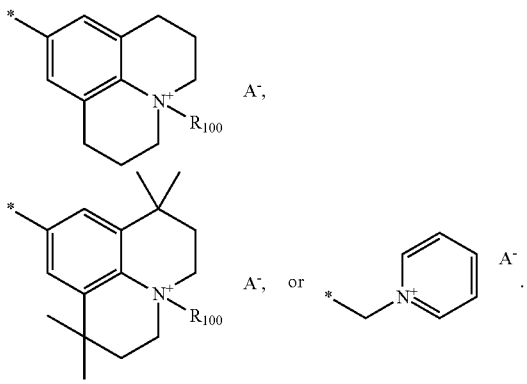

The anion $A^-$ is preferably RCOO$^-$, ClO$_4^-$, BF$_4^-$, PF$_6^-$, RSO$_3^-$, RSO$_4^-$ (preferably CF$_3$SO$_3^-$), SO$_4^{2-}$, OCN$^-$, SCN$^-$, NO$_3^-$, F$^-$, Cl$^-$, Br$^-$, I$^-$, RO$^-$, ClO$_4^-$, HSO$_4^{2-}$, PO$_4^{3-}$, HPO$_4^{2-}$, H$_2$PO$_4^{2-}$, CO$_3^{2-}$ or HCO$_3^-$, with R being hydrogen, unsubstituted or optionally substituted $C_1$-$C_{18}$alkyl More preferably $A^-$ is RSO$_3^-$, OCN$^-$, SCN$^-$, NO$_3^-$, F$^-$, I$^-$ and Cl$^-$. Most preferably $A^-$ is Cl$^-$.

For example the catalyst is of formula (3) or (4)

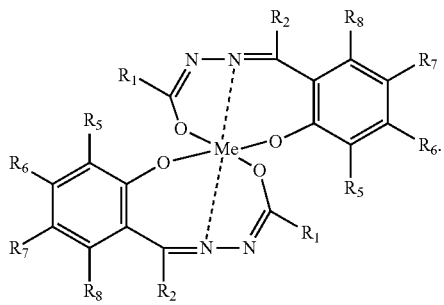

wherein

Me is manganese in oxidation states II-V or iron in oxidation states I to IV;

X is CH$_3$CN, H$_2$O, F$^-$, Cl$^-$, Br$^-$, HOO$^-$, O$_2^{2-}$, O$^{2-}$, R$_{28}$COO$^-$, R$_{28}$O$^-$;

$R_{28}$ is hydrogen, unsubstituted or substituted $C_1$-$C_{18}$alkyl or phenyl;

p is an integer from 1 to 4;

$R_1$ is —$(CH_2)_k$—$N^+(R_{100}R'_{100}R''_{100})_3 A^-$, wherein $A^-$ is an anion and k is a number from 1 to 4; or phenyl substituted with 1 to 5 electron withdrawing substituents;

$R_2$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl;

$R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl; —OR$_{100}$, —NR$_{100}$R'$_{100}$, halogen; or independently have the meaning as defined for $R_1$; or $R_5$ and $R_6$, $R_6$ and $R_7$ and/or $R_7$ and $R_8$, may be linked together to form 1, 2 or 3 carbocyclic or heterocyclic rings, which may be uninterrupted or interrupted by one or more —O—, —S— or —NR$_9$— and/or which may be further fused with other aromatic rings and/or which may be substituted with one or more $C_1$-$C_6$alkyl groups.

In a specific embodiment of the invention the catalyst is of formula (3) or (4)

(4)

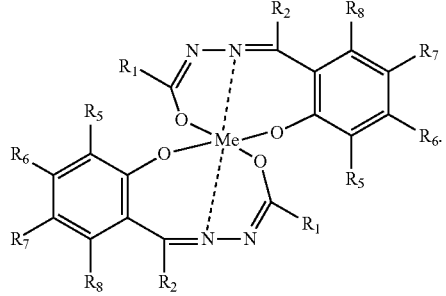

wherein

Me is manganese in oxidation states II-V or iron in oxidation states I to IV;

X is $CH_3CN$, $H_2O$, $F^-$, $Cl^-$, $Br^-$, $HOO^-$, $O_2^{2-}$, $O^{2-}$, $R_{28}COO^-$, $R_{28}O^-$;

$R_{28}$ is hydrogen, unsubstituted or substituted $C_1$-$C_{18}$alkyl or phenyl;

p is an integer from 1 to 4;

$R_1$ is —$(CH_2)_k$—$N^+(R_{100}R'_{100}R''_{100})_3 A^-$, wherein $A^-$ is an anion and k is a number from 1 to 4; or phenyl substituted with 1 to 5 electron withdrawing substituents selected from the group consisting of
—$OC(O)OR_{100}$, —$COOR_{100}$, —$C(O)$—$R_{100}$, —CN, —$NO_2$, —$SO_3R_{100}$, —$CF_3$, F, Cl, Br, I, —$N(R_{100}R'_{100}R''_{100})_3{}^+A^-$, —$N(R_{101}R'_{101})$ and

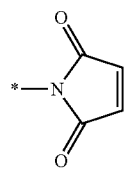

wherein $R_{100}$, $R'_{100}$, $R''_{100}$ are independently hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; * is the point of attachment and $A^-$ is an anion, $R_{101}$, $R'_{101}$ independently are —$C(O)$—$R_{100}$, —$C(O)N(R_{100}R'_{100})$ or —$C(O)OR_{100}$;

or $R_1$ together with the electron withdrawing substituent is a group

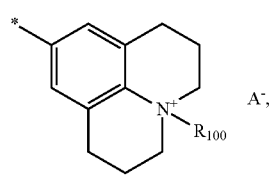

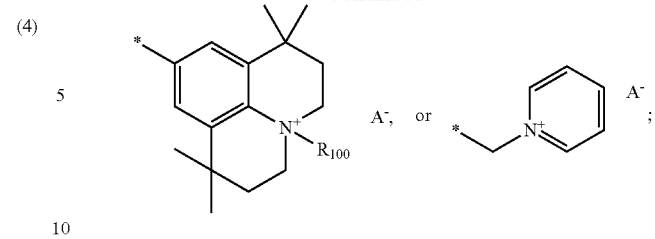

$R_2$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl;

$R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl; —$OR_{100}$, —$NR_{100}R'_{100}$, halogen; or independently have the meaning as defined for $R_1$; or $R_5$ and $R_6$, $R_6$ and $R_7$ and/or $R_7$ and $R_8$, may be linked together to form 1, 2 or 3 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups.

Examples of suitable anions $A^-$ have already been given above. Most preferred is $Cl^-$.

Particularly preferred is $R_1$ in the meaning of phenyl substituted with 1 to 5 electron withdrawing substituents selected from the group consisting of
—$OC(O)OR_{100}$, —$COOR_{100}$, —$C(O)$—$R_{100}$, —CN, —$NO_2$, —$SO_3R_{100}$, —$CF_3$, F, Cl, Br, I, —$N(R_{100}R'_{100}R''_{100})_3{}^+A^-$, —$N(R_{101}R'_{101})$ and

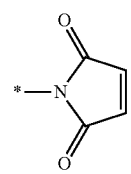

wherein $R_{100}$, $R'_{100}$, $R''_{100}$ are independently hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; * is the point of attachment and $A^-$ is an anion, $R_{101}$, $R'_{101}$ independently are —$C(O)$—$R_{100}$, —$C(O)N(R_{100}R'_{100})$ or —$C(O)OR_{100}$;

or $R_1$ together with the electron withdrawing substituent is a group

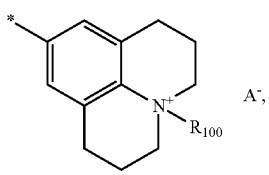

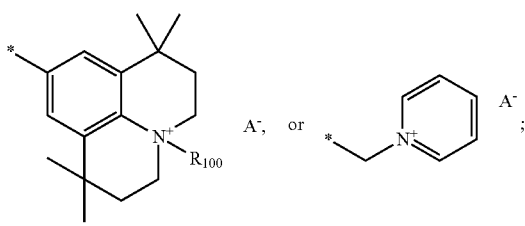

In another preferred embodiment $R_1$ has the meaning of —$(CH_2)_k$—$N^+(CH_3)_3A^-$. Definitions for the substituents have already been given above.

The $R_5$-$R_8$ in both phenyl rings can be selected independently from the definitions given above and, for example, $R_5$ in one ring can have a different meaning from the $R_5$ in the other ring. This applies equally to the $R_6$ to $R_8$.

Preferably Me is manganese in oxidation states II-V or iron in oxidation states I to IV;

X is $H_2O$, $F^-$, $Cl^-$, $Br^-$, $HOO^-$, $R_{28}COO^-$ or $R_{28}O^-$;

$R_{28}$ is hydrogen, unsubstituted or substituted $C_1$-$C_{18}$alkyl;

p is an integer 1 or 2;

$R_1$ is phenyl substituted with 1 to 5 electron withdrawing substituents selected from the group consisting of —$OR_{100}$, —$COOR_{100}$, —$C(O)$—$R_{100}$, —CN, —$NO_2$, —$SO_3R_{100}$, —$CF_3$, F, Cl, Br, I, —$N(R_{100}R'_{100}R''_{100})_3^+A^-$, —$N(R_{101}R'_{101})$ or

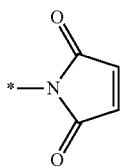

wherein $R_{100}$, $R'_{100}$, $R''_{100}$ are independently hydrogen, $C_1$-$C_{18}$alkyl or phenyl, * is the point of attachment and $A^-$ is an anion;

$R_{101}$, $R'_{101}$ independently are —C(O)—$R_{100}$, —C(O)N($R_{100}R'_{100}$) or —C(O)O$R_{100}$;

$R_2$, $R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl; —$OR_{100}$, —$NR_{100}R'_{100}$, halogen; or independently have the meaning as defined for $R_1$.

In a specific embodiment of the invention the integers m and p in formula (1) are 0 and the ligand L of formula (2) is used as a catalyst for oxidation reactions;

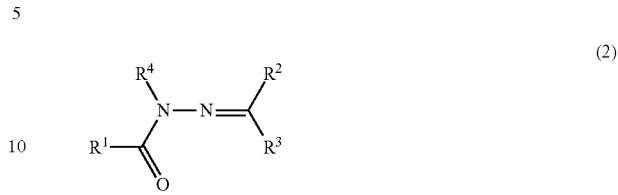

wherein the substituents are as defined above including their preferences.

Surprisingly it has been found that the ligands alone can also be used as catalysts for oxidation reactions for example in a washing process.

The complex compounds of formula (1) or the pure ligands of formula (2) are used as catalysts together with peroxide or a peroxide-forming substance, $O_2$ and/or air for the bleaching of stains or of soiling on textile material in the context of a washing process or by the direct application of a stain remover; for the cleaning of hard surfaces, especially kitchen surfaces, wall tiles or floor tiles; for the use in automatic dishwashing compositions; for the bleaching of stains or of soiling on textile material by atmospheric oxygen, whereby the bleaching is catalysed during and/or after the treatment of the textile in the washing liquor; for the prevention of redeposition of migrating dyes during the washing of textile material; for the use in washing and cleaning solutions having an antibacterial action; as pretreatment agents for bleaching textiles; as catalysts in selective oxidation reactions in the context of organic synthesis; for the waste water treatment; for bleaching in the context of paper-making; for sterilization; and for contact lens disinfection.

Another aspect of the invention is a process for the bleaching of stains or of soiling on textile materials in the context of a washing process or by the direct application of a stain remover and for the cleaning of hard surfaces comprising bringing into contact a textile material or hard surface material in an aqueous medium, a complex compound of formula (1) or a ligand of formula (2) as described above and a peroxide or a peroxide-forming substance or $O_2$ and/or air.

The ligands can be prepared according to standard procedures by reacting a carbonyl compound, such as an aldehyde with a primary amine to form the corresponding Schiff base, in particular with a hydrazide of formula (6) with a carbonyl compound of formula (7) wherein the substituents are as defined above.

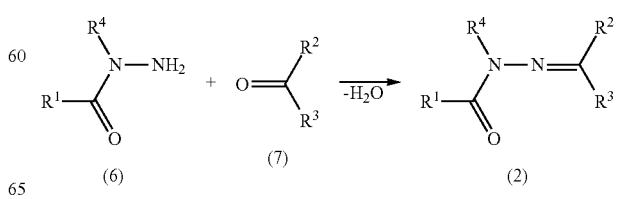

Individual ligands are summarized in the following table.
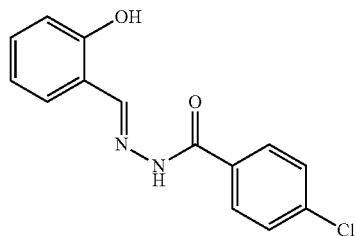
L1
E/Z-isomers and tautomeric forms
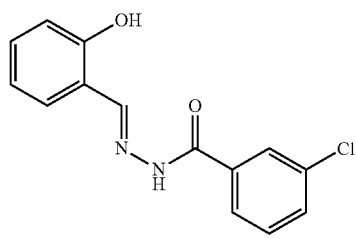
L2
E/Z-isomers and tautomeric forms
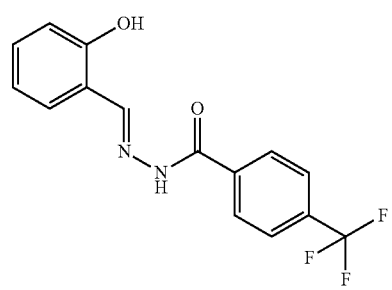
L7
E/Z-isomers and tautomeric forms
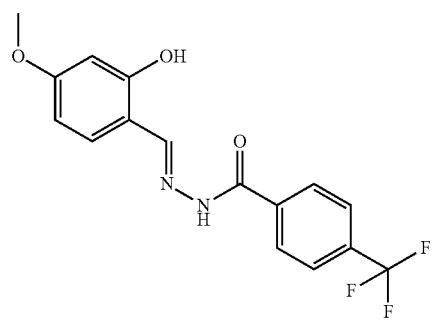
L8
E/Z-isomers and tautomeric forms
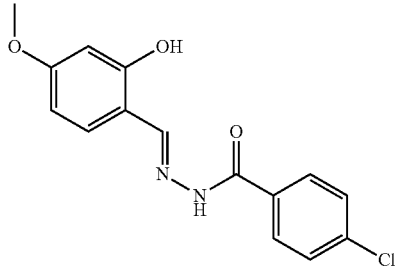
L3
E/Z-isomers and tautomeric forms
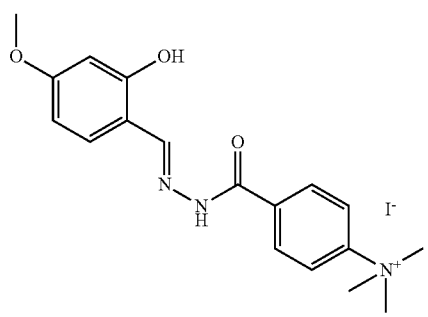
L9
E/Z-isomers and tautomeric forms
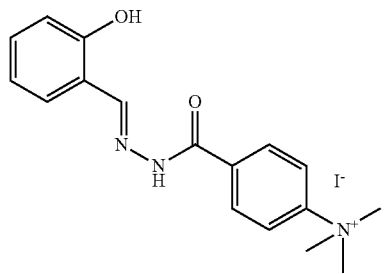
L10
E/Z-isomers and tautomeric forms
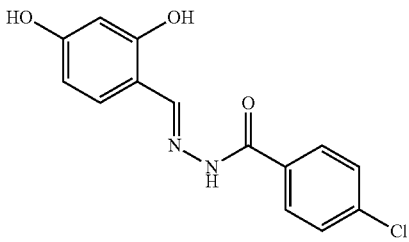
L4
E/Z-isomers and tautomeric forms -continued
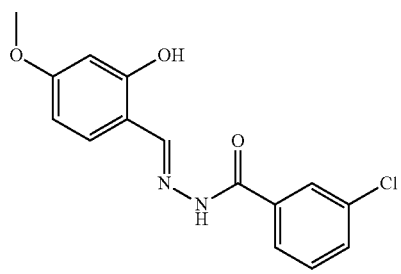
E/Z-isomers and tautomeric forms
L6
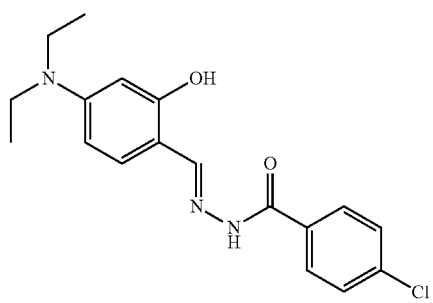
E/Z-isomers and tautomeric forms
L5
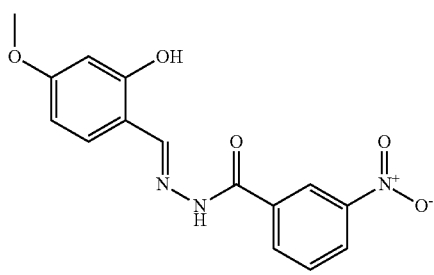
E/Z-isomers and tautomeric forms
L11
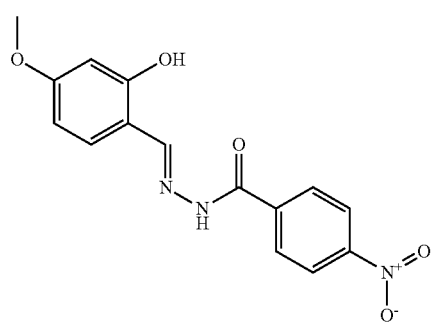
E/Z-isomers and tautomeric forms
L13
-continued
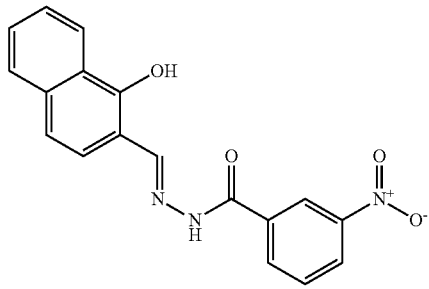
E/Z-isomers and tautomers
L44
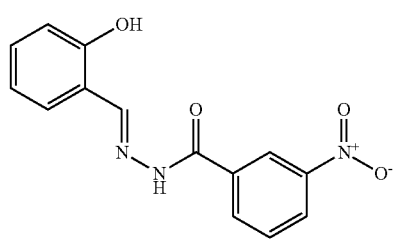
E/Z-isomers and tautomeric forms
L12
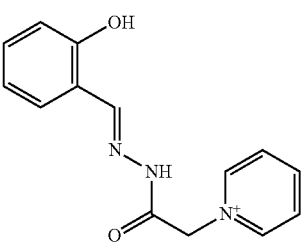
E/Z-isomers and tautomers
L57
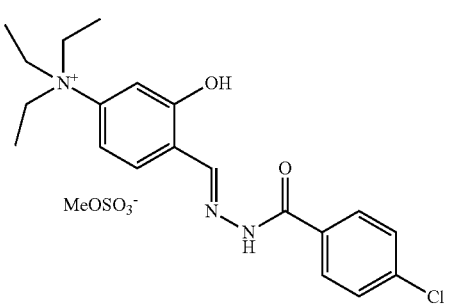
E/Z-isomers and tautomeric forms
L20

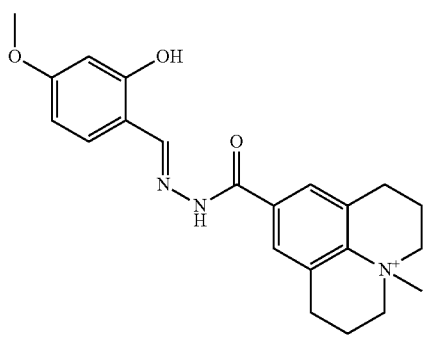
L23
E/Z-isomers and tautomeric forms
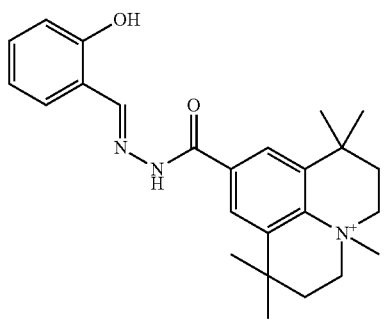
L24
E/Z-isomers and tautomeric forms
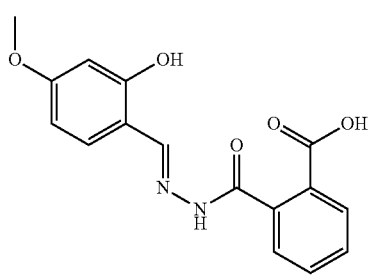
L60
E/Z-isomers and tautomers
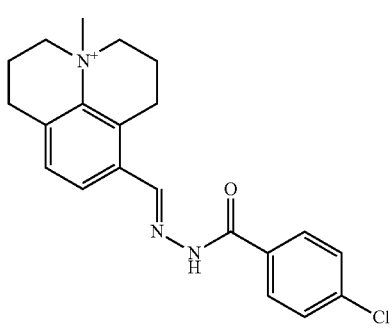
L26
E/Z-isomers and tautomeric forms
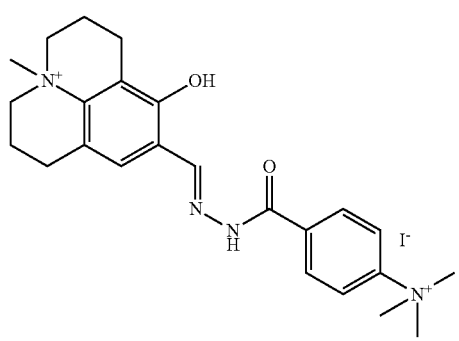
L27
E/Z-isomers and tautomeric forms
L28
E/Z-isomers and tautomeric forms
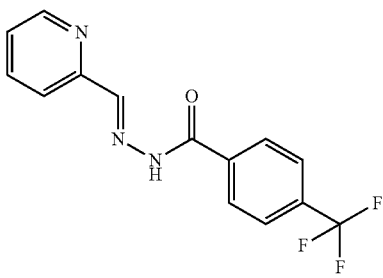
L29
E/Z-isomers and tautomeric forms
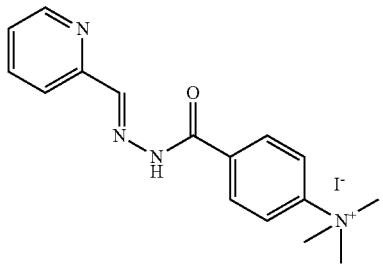
L30
E/Z-isomers and tautomeric forms -continued
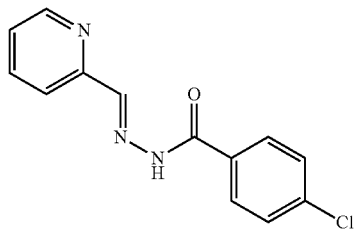
L31
E/Z-isomers and tautomeric forms
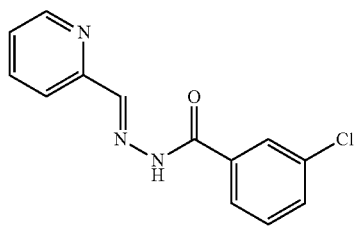
L32
E/Z-isomers and tautomeric forms
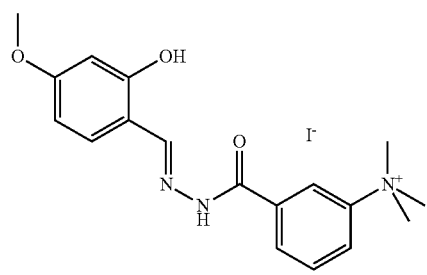
L33
E/Z-isomers and tautomeric forms
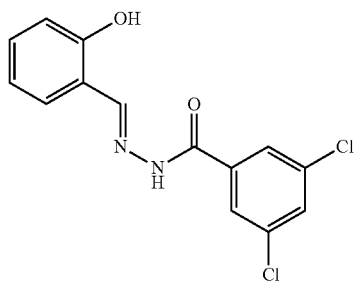
L34
E/Z-isomers and tautomeric forms
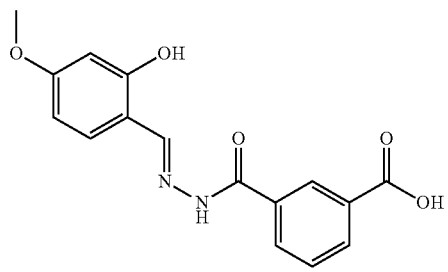
L35
E/Z-isomers and tautomeric forms
-continued
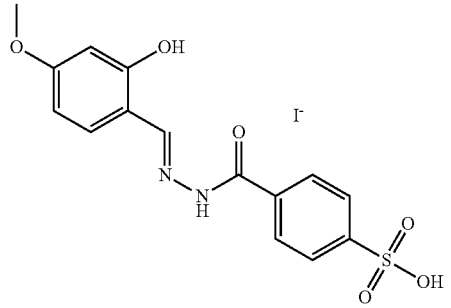
L36
E/Z-isomers and tautomeric forms
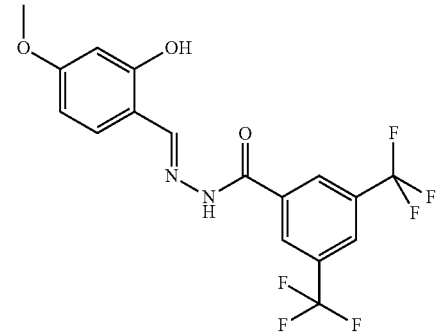
L37
E/Z-isomers and tautomers
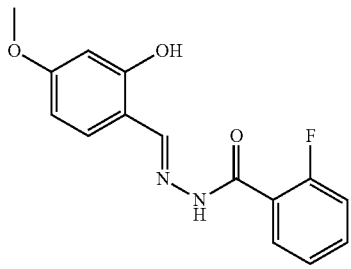
L38
E/Z-isomers and tautomers
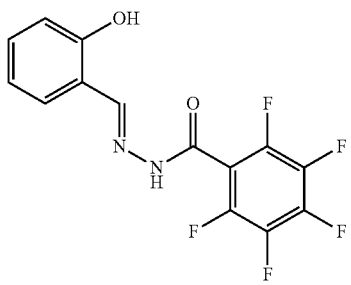
L39
E/Z-isomers and tautomeric forms

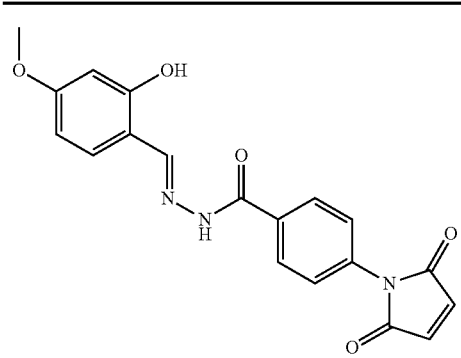
L40
E/Z-isomers and tautomers
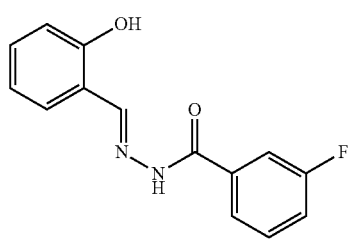
L63
E/Z-isomers and tautomeric forms
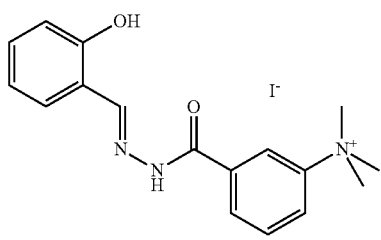
L56
E/Z-isomers and tautomeric forms
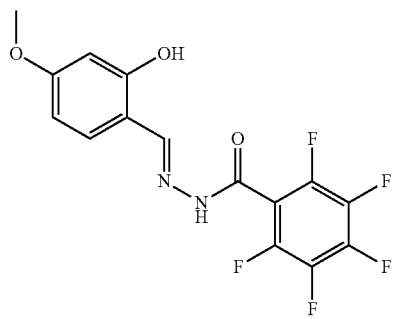
L64
E/Z-isomers and tautomeric forms
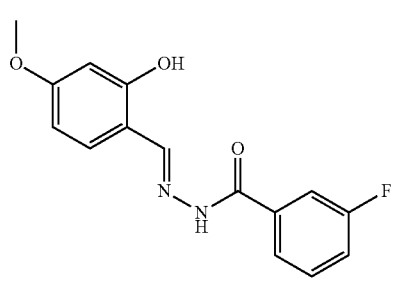
L46
E/Z-isomers and tautomers
L65
E/Z-isomers and tautomeric forms
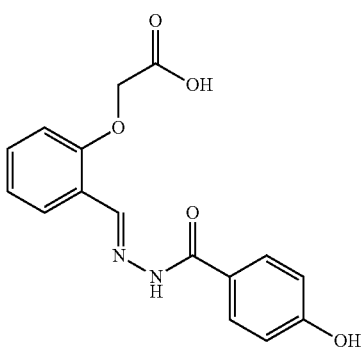
L50
E/Z-isomers and tautomers
L51
E/Z-isomers and tautomeric forms

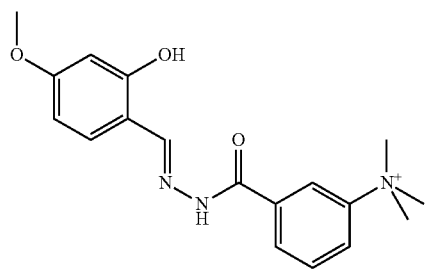

L52

E/Z-isomers and tautomeric forms

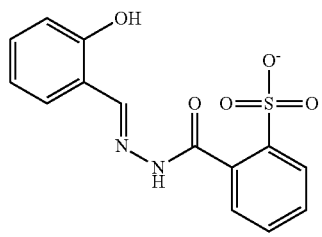

L53

E/Z-isomers and tautomers

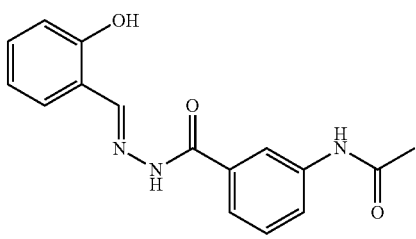

L54

E/Z-isomers and tautomers

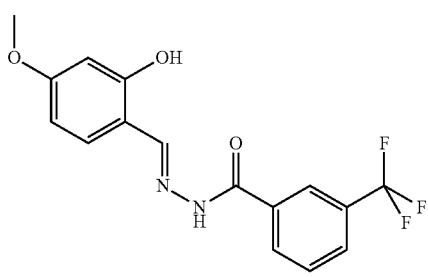

L66

E/Z-isomers and tautomeric forms

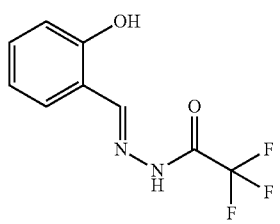

L16

E/Z-isomers and tautomers

It will be appreciated that the complex (1) can be formed by any appropriate means, including in situ formation whereby precursors of the complex are transformed into the active complex of general formula (1) under conditions of storage or use. Preferably, the complex is formed as a well-defined complex or in a solvent mixture comprising a salt of the metal Me and the ligand L or ligand L-generating species. Alternatively, the catalyst may be formed in situ from suitable precursors for the complex, for example in a solution or dispersion containing the precursor materials. In one such example, the active catalyst may be formed in situ in a mixture comprising a salt of the metal Me and the ligand L, or a ligand L-generating species, in a suitable solvent. Thus, for example, if Me is manganese, an manganese salt such as $MnCl_2$ or $Mn(OOCCH_3)_2$ can be mixed in solution with the ligand L, or a ligand L-generating species, to form the active complex. Such synthesis procedures are for example described in Inorganica Chimica Acta (1974), 9(2), 137-42; Monatshefte fuer Chemie (1976), 107(6), 1455-62; Transition Metal Chemistry (Dordrecht, Netherlands) (1977), 2(1), 29-30; Inorganica Chimica Acta (2007), 360(5), 1599-1608; Malaysian Journal of Science, 25(1), 107-114; 2006; Pestycydy (Warsaw), (1-2), 21-31; 2004 or in Journal of the Indian Chemical Society, 81(11), 950-953; 2004.

In another such example, the ligand L, or a ligand L-generating species, can be mixed with metal Me ions present in the substrate or wash liquor to form the active catalyst in situ. Suitable ligand L-generating species include metal-free compounds or metal coordination complexes that comprise the ligand L and can be substituted by metal Me ions to form the active complex according to formula (1).

The metal complex compounds of formula (1) or the ligands of formula (2) are used together as catalysts with peroxide or a peroxide-forming substance, $O_2$ and/or air. Examples that may be mentioned in that regard include the following uses:

a) the bleaching of stains or of soiling on textile material in the context of a washing process or by the direct application of a stain remover;
b) the cleaning of hard surfaces, especially kitchen surfaces, wall tiles or floor tiles, for example to remove stains that have formed as a result of the action of moulds ("mould stains"); the use in automatic dishwashing compositions is also a preferred use;
c) the bleaching of stains or of soiling on textile material by atmospheric oxygen, whereby the bleaching is catalysed during and/or after the treatment of the textile in the washing liquor;
d) the prevention of redeposition of migrating dyes during the washing of textile material;
e) use in washing and cleaning solutions having an anti-bacterial action;
f) as pretreatment agents for bleaching textiles;
g) as catalysts in selective oxidation reactions in the context of organic synthesis;
h) waste water treatment;
i) use as a catalyst for reactions with peroxy compounds for bleaching in the context of paper-making. This relates especially to the delignification of cellulose and bleaching of the pulp, which can be carried out in accordance with customary procedures. Also of interest is the use as a catalyst for reactions with peroxy compounds for the bleaching of waste printed paper;
j) sterilisation and
k) contact lens disinfection.

Preference is given to the bleaching of stains or soiling on textile material; to the cleaning of hard surfaces, especially kitchen surfaces, wall tiles, floor tiles as well as the use in automatic dishwasher formulations; to the bleaching of stains or of soiling on textile material by atmospheric oxygen, whereby the bleaching is catalysed during and/or after the treatment of the textile in the washing liquor; or to the prevention of redeposition of migrating dyes in the context of a washing process.

The preferred metals for these uses are manganese and/or iron, in particular manganese.

It should be emphasised that the use of metal complex compounds, for example, in the bleaching of textile or hard surface material, does not cause any appreciable damage to fibres and dyeings as well as to the hard surface materials, such as table- and kitchen-ware, as well as tiles.

Processes for bleaching stains in any washing liquor are usually carried out by adding to the washing liquor (with $H_2O_2$ or a precursor of $H_2O_2$) one or more metal complex compounds of formula (1). Alternatively, it is possible to add a detergent that already comprises one or two metal complex compounds. It will be understood that in such an application, as well as in the other applications, the metal complex compounds of formula (1) can alternatively be formed in situ, the metal salt (e.g. manganese(II) salt, such as manganese(II) chloride, and/or iron(II) salt, such as iron(II) chloride) and the ligand being added in the desired molar ratios.

Consequently a further aspect of the invention is a detergent, cleaning, disinfecting or bleaching composition comprising I) from 0 to 50 wt-%, based on the total weight of the composition, A) of at least one anionic surfactant and/or B) of a non-ionic surfactant,
II) from 0 to 70 wt-%, based on the total weight of the composition, C) of at least one builder substance,
III) from 1-99 wt-%, based on the total weight of the composition, D) of at least one peroxide and/or one peroxide-forming substance, $O_2$ and/or air,
IV) E) at least one metal complex compound of formula (1) or a ligand of formula (2) as defined above in an amount that, in the liquor, gives a concentration of from 0.5 to 100 mg/liter of liquor, when from 0.5 to 50 g/liter of the detergent, cleaning, disinfecting or bleaching agent are added to the liquor,
V) from 0-20 wt-%, based on the total weight of the composition, of at least one further additive, and
VI) water ad 100 wt-%, based on the total weight of the composition.

Preferably such a composition is used for a textile material or a hardsurface material.

All wt-% are based on the total weight of the detergent, cleaning, disinfecting or bleaching composition.

The detergent, cleaning, disinfecting or bleaching composition can be any kind of industrial or domestic cleaning, disinfecting or bleaching formulation.

It can be used for example in compositions used for textile material as well as in composition used for hardsurfaces, such as hard surface materials, such as table- and kitchen-ware, as well as tiles.

Preferred hard surface cleaning compositions are dishwashing detergent formulations, more preferably automatic dishwashing detergent formulations.

The above percentages are in each case percentage by weight, based on the total weight of the composition. The compositions preferably contain from 0.005 to 2 wt-% of at least one metal complex compound of formula (1), more preferably from 0.01 to 1 wt-% and most preferably from 0.05 to 1 wt-%.

When the compositions according to the invention comprise a component A) and/or B), the amount thereof is preferably from 1 to 50 wt-%, especially from 1 to 30 wt-%.

When the compositions according to the invention comprise a component C), the amount thereof is preferably from 1 to 70 wt-%, especially from 1 to 50 wt-%. Special preference is given to an amount of from 5 to 50 wt-% and especially an amount of from 10 to 50 wt-%.

Corresponding washing, cleaning, disinfecting or bleaching processes are usually carried out by using an aqueous liquor containing from 0.1 to 200 mg of one or more compounds of formula (1) per liter of liquor. The liquor preferably contains from 1 to 50 mg of at least one compound of formula (1) per liter of liquor.

The composition according to the invention can be, for example, a peroxide-containing heavy-duty detergent or a separate bleaching additive, or a stain remover that is to be applied directly. A bleaching additive is used for removing coloured stains on textiles in a separate liquor before the clothes are washed with a bleach-free detergent. A bleaching additive can also be used in a liquor together with a bleach-free detergent.

Stain removers can be applied directly to the textile in question and are used especially for pretreatment in the event of heavy local soiling.

The stain remover can be applied in liquid form, by a spraying method or in the form of a solid substance, such as a powder especially as a granule.

Granules can be prepared, for example, by first preparing an initial powder by spray-drying an aqueous suspension comprising all the components listed above except for component E), and then adding the dry component E) and mixing everything together. It is also possible to add component E) to an aqueous suspension containing components A), B), C) and D) and then to carry out spray-drying.

It is also possible to start with an aqueous suspension that contains components A) and C), but none or only some of component B). The suspension is spray-dried, then component E) is mixed with component B) and added, and then component D) is mixed in the dry state. It is also possible to mix all the components together in the dry state.

The anionic surfactant A) can be, for example, a sulfate, sulfonate or carboxylate surfactant or a mixture thereof. Preference is given to alkylbenzenesulfonates, alkyl sulfates, alkyl ether sulfates, olefin sulfonates, fatty acid salts, alkyl and alkenyl ether carboxylates or to an α-sulfonic fatty acid salt or an ester thereof.

Preferred sulfonates are, for example, alkylbenzenesulfonates having from 10 to 20 carbon atoms in the alkyl radical, alkyl sulfates having from 8 to 18 carbon atoms in the alkyl radical, alkyl ether sulfates having from 8 to 18 carbon atoms in the alkyl radical, and fatty acid salts derived from palm oil or tallow and having from 8 to 18 carbon atoms in the alkyl moiety. The average molar number of ethylene oxide units added to the alkyl ether sulfates is from 1 to 20, preferably from 1 to 10. The cation in the anionic surfactants is preferably an alkaline metal cation, especially sodium or potassium, more especially sodium. Preferred carboxylates are alkali metal sarcosinates of formula $R_{19}$—$CON(R_{20})CH_2COOM_1$ wherein $R_{19}$ is $C_9$-$C_{17}$alkyl or $C_9$-$C_{17}$alkenyl, $R_{20}$ is $C_1$-$C_4$alkyl and $M_1$ is an alkali metal, especially sodium.

The non-ionic surfactant B) may be, for example, a primary or secondary alcohol ethoxylate, especially a $C_8$-$C_{20}$ aliphatic alcohol ethoxylated with an average of from 1 to 20 mol of ethylene oxide per alcohol group. Preference is given to primary and secondary $C_{10}$-$C_{15}$ aliphatic alcohols ethoxylated with an average of from 1 to 10 mol of ethylene oxide per alcohol group. Non-ethoxylated non-ionic surfactants, for example alkylpolyglycosides, glycerol monoethers and polyhydroxyamides (glucamide), may likewise be used.

The total amount of anionic and non-ionic surfactants is preferably from 5 to 50 wt-%, especially from 5 to 40 wt-% and more especially from 5 to 30 wt-%. The lower limit of those surfactants to which even greater preference is given is 10 wt-%.

In addition to anionic and/or non-ionic surfactants the composition may contain cationic surfactants. Possible cationic surfactants include all common cationic surface-active compounds, especially surfactants having a textile softening effect.

Non-limited examples of cationic surfactants are given in the formulas below:

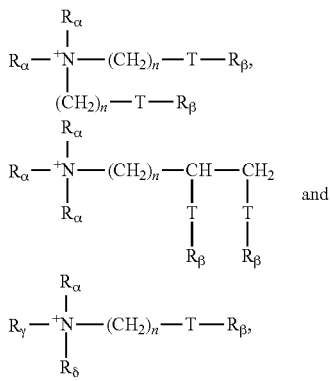

wherein
each radical $R_\alpha$ is independent of the others $C_{1-6}$-alkyl-, -alkenyl- or -hydroxyalkyl; each
radical $R_\beta$ is independent of the others $C_{8-28}$-alkyl- or alkenyl;
$R_\gamma$ is $R_\alpha$ or $(CH_2)_n$-T-$R_\beta$;
$R_\delta$ is $R_\alpha$ or $R_\beta$ or $(CH_2)_n$-T-$R_\beta$; T=—$CH_2$—, —O—CO— or —CO—O— and
n is between 0 and 5.

Preferred cationic surfactants present in the composition according to the invention include hydroxyalkyl-trialkyl-ammonium-compounds, especially $C_{12-18}$-alkyl(hydroxyethyl) dimethylammonium compounds, and especially preferred the corresponding chloride salts. Compositions of the present invention can contain between 0.5 wt-% and 15 wt-% of the cationic surfactant, based on the total weight of the composition.

As builder substance C) there come into consideration, for example, alkali metal phosphates, especially tripolyphosphates, carbonates and hydrogen carbonates, especially their sodium salts, silicates, aluminum silicates, polycarboxylates, polycarboxylic acids, organic phosphonates, aminoalkylenepoly(alkylenephosphonates) and mixtures of such compounds.

Silicates that are especially suitable are sodium salts of crystalline layered silicates of the formula $NaHSi_tO_{2t+1} \cdot pH_2O$ or $Na_2Si_tO_{2t+1} \cdot pH_2O$ wherein t is a number from 1.9 to 4 and p is a number from 0 to 20.

Among the aluminum silicates, preference is given to those commercially available under the names zeolite A, B, X and HS, and also to mixtures comprising two or more of such components. Special preference is given to zeolite A.

Among the polycarboxylates, preference is given to polyhydroxycarboxylates, especially citrates, and acrylates, and also to copolymers thereof with maleic anhydride. Preferred polycarboxylic acids are nitrilotriacetic acid, ethylenediaminetetraacetic acid and ethylenediamine disuccinate either in racemic form or in the enantiomerically pure (S,S) form.

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid and diethylenetriaminepentamethylenephosphonic acid, and also salts thereof. Also preferred polyphosphonates have the following formula

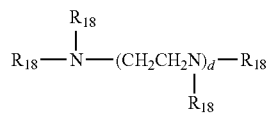

wherein
$R_{18}$ is $CH_2PO_3H_2$ or a water soluble salt thereof and
d is an integer of the value 0, 1, 2 or 3.

Especially preferred are the polyphosphonates wherein b is an integer of the value of 1.

The amount of the peroxide or the peroxide-forming substance is preferably 0.5-30 wt-%, more preferably 1-20 wt-% and especially preferably 1-15 wt-%.

As the peroxide component D) there come into consideration every compound which is capable of yielding hydrogen peroxide in aqueous solutions, for example, the organic and inorganic peroxides known in the literature and available commercially that bleach textile materials at conventional washing temperatures, for example at from 10 to 95° C.

Preferably, however, inorganic peroxides are used, for example persulfates, perborates, percarbonates and/or persilicates.

Example of suitable inorganic peroxides are sodium perborate tetrahydrate or sodium perborated monohydrate, sodium percarbonate, inorganic peroxyacid compounds, such as for example potassium monopersulphate (MPS). If organic or inorganic peroxyacids are used as the peroxygen compound, the amount thereof will normally be within the range of about 2-80 wt-%, preferably from 4-30 wt-%.

The organic peroxides are, for example, mono- or polyperoxides, urea peroxides, a combination of a $C_1$-$C_4$alkanol oxidase and $C_1$-$C_4$alkanol (Such as methanol oxidase and ethanol as described in WO95/07972), alkylhydroxy peroxides, such as cumene hydroperoxide and t-butyl hydroperoxide.

The peroxides may be in a variety of crystalline forms and have different water contents, and they may also be used together with other inorganic or organic compounds in order to improve their storage stability.

All these peroxy compounds may be utilized alone or in conjunction with a peroxyacid bleach precursor and/or an organic bleach catalyst not containing a transition metal. Generally, the bleaching composition of the invention can be suitably formulated to contain from 2 to 80 wt-%, preferably from 4 to 30 wt-%, of the peroxy bleaching agent.

As oxidants, peroxo acids can also be used. One example are organic mono peracids of formula

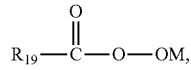

wherein

M signifies hydrogen or a cation, $R_{19}$ signifies unsubstituted $C_1$-$C_{18}$alkyl; substituted $C_1$-$C_{18}$alkyl; unsubstituted aryl; substituted aryl; —($C_1$-$C_6$alkylene)-aryl, wherein the alkylene and/or the alkyl group may be substituted; and phthalimido$C_1$-$C_8$alkylene, wherein the phthalimido and/or the alkylene group may be substituted.

Preferred mono organic peroxy acids and their salts are those of formula

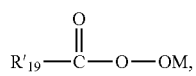

wherein

M signifies hydrogen or an alkali metal, and $R'_{19}$ signifies unsubstituted $C_1$-$C_4$alkyl; phenyl; —$C_1$-$C_2$alkylene-phenyl or phthalimido$C_1$-$C_8$alkylene.

Especially preferred is $CH_3COOOH$ and its alkali salts.

Especially preferred is also ε-phthalimido peroxy hexanoic acid and its alkali salts.

Also suitable are diperoxyacids, for example, 1,12-diperoxydodecanedioic acid (DPDA), 1,9-diperoxyazelaic acid, diperoxybrassilic acid, diperoxysebasic acid, diperoxyisophthalic acid, 2-decyldiperoxybutane-1,4-diotic acid and 4,4'-sulphonylbisperoxybenzoic acid.

Instead of the peroxy acid it is also possible to use organic peroxy acid precursors and $H_2O_2$. Such precursors are the corresponding carboxyacid or the corresponding carboxyanhydrid or the corresponding carbonylchlorid, or amides, or esters, which can form the peroxy acids on perhydrolysis. Such reactions are commonly known.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412,934 and 4,675,393.

Peroxy acids precursers are often referred to as bleach activators. Suitable bleach activators include the bleach activators, that carry O- and/or N-acyl groups and/or unsubstituted or substituted benzoyl groups. Preference is given to polyacylated alkylenediamines, especially tetraacetylethylenediamine (TAED); acylated glycolurils, especially tetraacetyl glycol urea (TAGU), N,N-diacetyl-N,N-dimethylurea (DDU); sodium-4-benzoyloxy benzene sulphonate (SBOBS); sodium-1-methyl-2-benzoyloxy benzene-4-sulphonate; sodium-4-methyl-3-benzoloxy benzoate; trimethyl ammonium toluoyloxy-benzene sulphonate; acylated triazine derivatives, especially 1,5-diacetyl-2,4-dioxohexahydro-1,3,5-triazine (DADHT); compounds of formula (6):

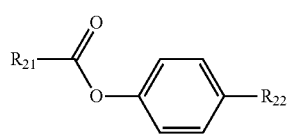

(10)

wherein $R_{22}$ is a sulfonate group, a carboxylic acid group or a carboxylate group, and wherein $R_{21}$ is linear or branched ($C_7$-$C_{15}$)alkyl, especially activators known under the names SNOBS, SLOBS and DOBA; acylated polyhydric alcohols, especially triacetin, ethylene glycol diacetate and 2,5-diacetoxy-2,5-dihydrofuran; and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A-44 43 177. Nitrile compounds that form perimine acids with peroxides also come into consideration as bleach activators.

Another useful class of peroxyacid bleach precursors is that of the cationic i.e. quaternary ammonium substituted peroxyacid precursors as disclosed in U.S. Pat. Nos. 4,751,015 and 4,397,757, in EP-A0284292 and EP-A-331,229. Examples of peroxyacid bleach precursors of this class are: 2-(N,N,N-trimethyl ammonium) ethyl sodium-4-sulphonphenyl carbonate chloride-(SPCC), N-octyl,N,N-dimethyl-N10-carbophenoxy decyl ammonium chloride—(ODC), 3-(N,N,N-trimethyl ammonium)propyl sodium-4-sulphophenyl carboxylate and N,N,N-trimethyl ammonium toluoyloxy benzene sulphonate.

A further special class of bleach precursors is formed by the cationic nitriles as disclosed in EP-A-303,520, WO 96/40661 and in European Patent Specification No.'s 458, 396, 790244 and 464,880. These cationic nitriles also known as nitril quats have the formula

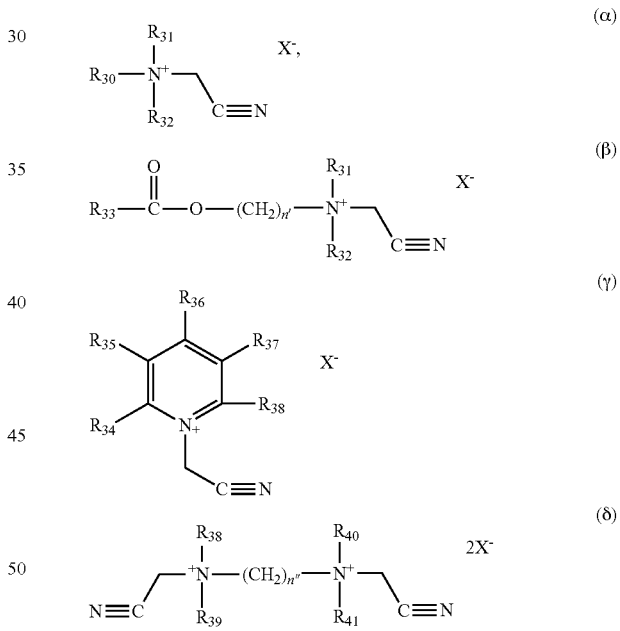

wherein $R_{30}$ is a $C_1$-$C_{24}$alkyl; a $C_1$-$C_{24}$alkenyl; an alkaryl having a $C_1$-$C_{24}$alkyl; a substituted $C_1$-$C_{24}$alkyl; a substituted $C_1$-$C_{24}$alkenyl; a substituted aryl, $R_{31}$ and $R_{32}$ are each independently a $C_1$-$C_3$alkyl; hydroxyalkyl having 1 to 3 carbon atoms, —($C_2H_4O)_nH$, n being 1 to 6; —$CH_2$—$CN$ $R_{33}$ is a $C_1$-$C_{20}$alkyl; a $C_1$-$C_{20}$alkenyl; a substituted $C_1$-$C_{20}$alkyl; a substituted $C_1$-$C_{20}$alkenyl; an alkaryl having a $C_1$-$C_{24}$alkyl and at least one other substituent, $R_{34}$, $R_{35}$, $R_{36}$, $R_{37}$ and $R_{38}$ are each independently hydrogen, a $C_1$-$C_{10}$alkyl, a $C_1$-$C_{10}$alkenyl, a substituted $C_1$-$C_{10}$alkyl, a substituted $C_1$-$C_{10}$alkenyl, carboxyl, sulfonyl or cyano $R_{38}$, $R_{39}$, $R_{40}$ and $R_{41}$ are each independently a $C_1$-$C_6$alkyl,
n' is an integer from 1 to 3,
n" is an integer from 1 to 16, and
X is an anion.

Other nitril quats have the following formula

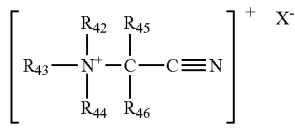
(ε)

wherein
$R_{42}$ and $R_{43}$ form, together with the nitrogen atom to which they are bonded, a ring comprising 4 to 6 carbon atoms, this ring may also be substituted by $C_1$-$C_5$-alkyl, $C_1$-$C_5$-alkoxy, $C_1$-$C_5$-alkanoyl, phenyl, amino, ammonium, cyano, cyanamino or chloro and 1 or 2 carbon atom(s) of this ring may also be substituted by a nitrogen atom, by a oxygen atom, by a N—$R_{47}$-group and/or by a $R_{44}$—N—$R_{47}$-group, wherein $R_{47}$ is hydrogen, $C_1$-$C_5$-alkyl, $C_2$-$C_5$-alkenyl, $C_2$-$C_5$-alkinyl, phenyl, $C_7$-$C_9$-aralkyl, $C_5$-$C_7$-Cycloalkyl, $C_1$-$C_5$-alkanoyl, cyanomethyl or cyano,
$R_{44}$ is $C_1$-$C_{24}$-, preferably $C_1$-$C_4$-alkyl; $C_2$-$C_{24}$-alkenyl, preferably $C_2$-$C_4$-alkenyl, cyanomethyl or $C_1$-$C_4$-alkoxy-$C_1$-$C_4$-alkyl,
$R_{45}$ and $R_{46}$ are independently from each other hydrogen; $C_1$-$C_4$-alkyl; $C_1$-$C_4$-alkenyl; $C_1$-$C_4$-alkoxy-$C_1$-$C_4$-alkyl; phenyl or $C_1$-$C_3$-alkylphenyl, preferably hydrogen, methyl or phenyl, whereby preferably the moiety $R_{45}$ signifies hydrogen, if $R_{46}$ is not hydrogen, and
$X^-$ is an anion.

Suitable examples of nitril quats of formula (ε) are

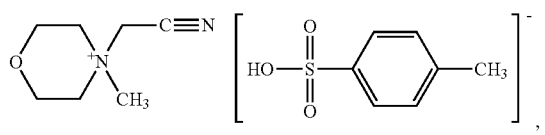

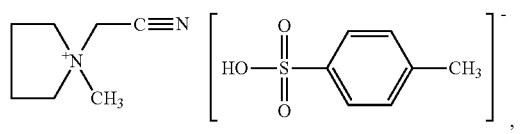

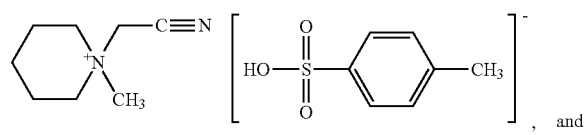
, and

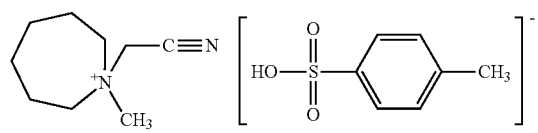

Other nitrile quats have the formula

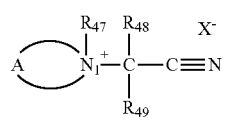
(φ)

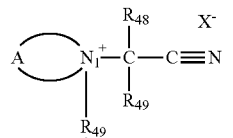
(η)

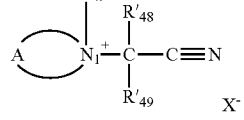

wherein
A is a saturated ring formed by a plurality of atoms in addition to the $N_1$ atom, the saturated ring atoms to include at least one carbon atom and at least one heteroatom in addition to the $N_1$ atom, the said one heteroatom selected from the group consisting of O, S and N atoms, the substituent $R_{47}$ bound to the $N_1$ atom of the Formula (φ) structure is (a) a $C_1$-$C_8$-alkyl or alkoxylated alkyl where the alkoxy is $C_{2-4}$, (b) a $C_4$-$C_{24}$cycloalkyl, (c) a $C_7$-$C_{24}$alkaryl, (d) a repeating or non-repeating alkoxy or alkoxylated alcohol, where the alkoxy unit is $C_{2-4}$, or (e) —$CR_{50}R_{51}$—C≡N where $R_{50}$ and $R_{51}$ are each H, a $C_1$-$C_{24}$alkyl, cycloalkyl, or alkaryl, or a repeating or nonrepeating alkoxyl or alkoxylated alcohol where the alkoxy unit is $C_2$-$C_4$, in Formula (φ) at least one of the $R_{48}$ and $R_{49}$ substituents is H and the other of $R_{48}$ and $R_{49}$ is H, a $C_1$-$C_{24}$alkyl, cycloalkyl, or alkaryl, or a repeating or nonrepeating alkoxyl or alkoxylated alcohol where the alkoxy unit is $C_{2-4}$, and Y is at least one counterion.

In a preferred embodiment of the invention the catalyst of formula (1) is used together with a peroxide or peroxide precursor and a bleach activator which is selected from the group consisting of tetraacetylethylenediamine, pentaacetylglucose, sodium octanoyloxybenzenesulfonate, sodium nonanoyloxybenzenesulfonate, sodium decanoyloxybenzenesulfonate, sodium undecanoyloxybenzenesulfonate, sodium dodecanoyloxybenzenesulfonate, octanoyloxybenzoic acid, nonanoyloxybenzoic acid, decanoyloxybenzoic acid, undecanoyloxybenzoic acid, dodecanoyloxybenzoic acid, octanoyloxybenzene, nonanoyloxybenzene, decanoyloxybenzene, undecanoyloxybenzene and dodecanoyloxybenzene.

The precursors may be used in an amount of up to 12 wt-%, preferably from 2-10 wt-% based on the total weight of the composition.

It is also possible to use further bleach catalysts, which are commonly known, for example transition metal complexes as disclosed in EP 1194514, EP 1383857 or WO04/007657. Further bleach catalysts are disclosed in: US2001044401, EP0458397, WO9606154, EP1038946, EP0900264, EP0909809, EP1001009, WO9965905, WO00248301, WO0060045, WO002077145, WO0185717, WO0164826, EP0923635, DE 19639603, DE102007017654, DE102007017657, DE102007017656, US20030060388, EP0918840B1, EP1174491A2, EP0805794B1, WO9707192A1, U.S. Pat. No. 6,235,695B1, EP0912690B1, EP832969B1, U.S. Pat. No. 6,479,450B1, WO9933947A1, WO0032731A1, WO003054128A1, DE102004003710, EP1083730, EP1148117, EP1445305, U.S. Pat. No. 6,476, 996, EP0877078, EP0869171, EP0783035, EP0761809 and EP1520910.

It is possible to use $H_2O_2$, $O_2$, air, the peroxy-containing compounds, the peroxy-acids as well as their precursors, further bleach catalyst and bleach activists in any combination with the inventive metal complexes.

The compositions may comprise, in addition to the combination according to the invention, one or more optical brighteners, for example from the classes bis-triazinylaminostilbenedisulfonic acid, bis-triazolyl-stilbenedisulfonic acid, bis-styryl-biphenyl or bis-benzofuranylbiphenyl, α bis-benzoxalyl derivative, bis-benzimidazolyl derivative or coumarin derivative or a pyrazoline derivative.

The compositions may furthermore comprise one or more further additives. Such additives are, for example, dirt-suspending agents, for example sodium carboxymethylcellulose; pH regulators, for example alkali metal or alkaline earth metal silicates; foam regulators, for example soap; salts for adjusting the spray drying and the granulating properties, for example sodium sulfate; perfumes; and also, if appropriate, antistatics and softening agents such as, for example, smectite; bleaching agents; pigments; and/or toning agents. These constituents should especially be stable to any bleaching agent employed.

If the detergent composition is used in an automatic dishwasher it is also common to use silver-corrosion inhibitors.

Such auxiliaries are added in a total amount of from 0.1-20 wt-%, preferably from 0.5-10 wt-%, especially from 0.5-5 wt-%, based on the total weight of the detergent formulation.

Furthermore, the detergent may optionally also comprise enzymes. Enzymes can be added for the purpose of stain removal. The enzymes usually improve the action on stains caused by protein or starch, such as, for example, blood, milk, grass or fruit juices. Preferred enzymes are cellulases and proteases, especially proteases. Cellulases are enzymes that react with cellulose and its derivatives and hydrolyse them to form glucose, cellobiose and cellooligosaccharides. Cellulases remove dirt and, in addition, have the effect of enhancing the soft handle of the fabric.

Examples of customary enzymes include, but are by no means limited to, the following:
proteases as described in U.S. Pat. No. 6,242,405, column 14, lines 21 to 32;
lipases as described in U.S. Pat. No. 6,242,405, column 14, lines 33 to 46;
amylases as described in U.S. Pat. No. 6,242,405, column 14, lines 47 to 56; and
cellulases as described in U.S. Pat. No. 6,242,405, column 14, lines 57 to 64.

Commercially available detergent proteases, such as Alcalase®, Esperase®, Everlase®, Savinase®, Kannase® and Durazym®, are sold e.g. by NOVOZYMES A/S.

Commercially available detergent amylases, such as Termamyl®, Duramyl®, Stainzyme®, Natalase®, Ban® and Fungamyl®, are sold e.g. by NOVOZYMES A/S.

Commercially available detergent ellulases, such as Celluzyme®, Carezyme® and Endolase®, are sold e.g. by NOVOZYMES A/S.

Commercially available detergent lipases, such as Lipolase®, Lipolase Ultra® and Lipoprime®, are sold e.g. by NOVOZYMES A/S.

Suitable mannanases, such as Mannanaway®, are sold by NOVOZYMES A/S.

Beside in laundry care products, in a hard surface cleaner, especially in a composition used in automatic dishwashers the following enzymes are also commonly used: proteases, amylases, pullulanases, cutinases and lipases, for example proteases such as BLAP®, Optimase®, Opticlean®, Maxacal®, Maxapem®, Esperase® and/or Savinase®, amylases such as Termamyl®, Amylase-LT®, Maxamyl® and/or Duramyl®, lipases such as Lipolase®, Lipomax®, Lumafast® and/or Lipozym®. The enzymes which may be used can, as described e.g. in International Patent Applications WO 92/11347 and WO 94/23005, be adsorbed on carriers and/or embedded in encapsulating substances in order to safeguard them against premature inactivation. They are present in the cleaning formulations according to the invention preferably in amounts not exceeding 5 wt-%, especially in amounts of from 0.1 wt-% to 1.2 wt-%.

Amylases: The present invention preferably makes use of amylases having improved stability in detergents, especially improved oxidative stability. Such amylases are non-limitingly illustrated by the following: (a) An amylase according to WO 94/02597, Novo Nordisk A/S, published Feb. 3, 1994, as further illustrated by a mutant in which substitution is made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens, B. subtilis*, or *B. stearothermophilus*; (b) Stability-enhanced amylases as described by Genencor International in a paper entitled "Oxidatively Resistant alpha-Amylases" presented at the 207th American Chemical Society National Meeting, Mar. 13-17, 1994, by C. Mitchinson. Therein it was noted that bleaches in automatic dishwashing detergents inactivate alpha-amylases but that improved oxidative stability amylases have been made by Genencor from *B. licheniformis* NCIB8061. Any other oxidative stability-enhanced amylase can be used. Proteases: Protease enzymes are usually present in preferred embodiments of the invention at levels between 0.001 wt-% and 5 wt-%. The proteolytic enzyme can be of animal, vegetable or microorganism (preferred) origin. More preferred is serine proteolytic enzyme of bacterial origin. Purified or nonpurified forms of enzyme may be used. Proteolytic enzymes produced by chemically or genetically modified mutants are included by definition, as are close structural enzyme variants. Suitable commercial proteolytic enzymes include Alcalase®, Esperase®, Durazyme®, Savinase®, Maxatase®, Maxacal®, and Maxapem® 15 (protein engineered Maxacal). Purafect® and subtilisin BPN and BPN' are also commercially available.

When present, lipases comprise from about 0.001 wt-% to about 0.01 wt-% of the instant compositions and are optionally combined with from about 1 wt-% to about 5 wt-% of a surfactant having limesoap-dispersing properties, such as an alkyldimethylamine N-oxide or a sulfobetaine. Suitable lipases for use herein include those of bacterial, animal and fungal origin, including those from chemically or genetically modified mutants.

When incorporating lipases into the instant compositions, their stability and effectiveness may in certain instances be enhanced by combining them with small amounts (e.g., less than 0.5 wt-% of the composition) of oily but non-hydrolyzing materials.

The enzymes, when used, may be present in a total amount of from 0.01 to 5 wt-%, especially from 0.05 to 5 wt-% and more especially from 0.1 to 4 wt-%, based on the total weight of the detergent formulation.

If the detergent formulation is a hard surface cleaning composition, preferably a dishwashing detergent formulation, more preferably an automatic dishwashing detergent formulation, then it can optionally also comprises from about 0.001 wt-% to about 10 wt-%, preferably from about 0.005 wt-% to about 8 wt-%, most preferably from about 0.01 wt-% to about 6 wt-% of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

In order to enhance the bleaching action, the compositions may, in addition to comprising the catalysts described herein, also comprise photocatalysts the action of which is based on the generation of singlet oxygen.

Further preferred additives to the compositions according to the invention are dye-fixing agents and/or polymers which, during the washing of textiles, prevent staining caused by dyes in the washing liquor that have been released from the textiles under the washing conditions. Such polymers are preferably polyvinylpyrrolidones, polyvinylimidazoles or polyvinylpyridine-N-oxides, which may have been modified by the incorporation of anionic or cationic substituents, especially those having a molecular weight in the range of from 5000 to 60 000, more especially from 10 000 to 50 000. Such polymers are usually used in a total amount of from 0.01 to 5 wt-%, especially from 0.05 to 5 wt-%, more especially from 0.1 to 2 wt-%, based on the total weight of the detergent formulation. Preferred polymers are those mentioned in WO-A-02/02865 (see especially page 1, last paragraph and page 2, first paragraph) and those in WO-A-04/05688.

When the inventive detergent composition is used as hard-surface cleaner, especially when the composition is used in automatic dishwasher formulation then, it has been found out, that it is preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions.

Other examples for foam suppressors are paraffin, paraffin/alcohol combinations, or bisfatty acid amides.

The hard surface cleaning compositions, preferably dishwashing detergent formulations, more preferably automatic dishwashing detergent formulations herein may also optionally contain one or more heavy metal chelating agents, such as hydroxyethyldiphosphonate (HEDP). More generally, chelating agents suitable for use herein can be selected from the group consisting of amino carboxylates, amino phosphonates, polyfunctionally-substituted aromatic chelating agents and mixtures thereof. Other suitable chelating agents for use herein are the commercial DEQUEST series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof and mixtures thereof.

Aminophosphonates are also suitable for use as chelating agents in the compositions of the invention when at least low levels of total phosphorus are permitted in detergent compositions, and include ethylenediaminetetrakis (methylenephosphonates).

Further biodegradable sequestrants are, for example, aminoacid acetates, such as Trilon M (BASF) and Dissolvine GL (AKZO), as well as asparaginic acid derivatives, such as Baypure CX.

Preferably, the aminophosphonates do not contain alkyl or alkenyl groups with more than about 6 carbon atoms.

A highly preferred biodegradable chelator for use herein is ethylenediamine disuccinate ("EDDS").

If utilized, these chelating agents or transition-metal selective sequestrants will generally comprise from about 0.001 wt-% to about 10 wt-%, more preferably from about 0.05 wt-% to about 1 wt-% of the hard surface cleaning compositions, preferably dishwashing detergent formulations, more preferably automatic dishwashing detergent formulations herein.

Preferred hard surface cleaning compositions, preferably dishwashing detergent formulations, more preferably automatic dishwashing detergent formulations herein may additionally contain a dispersant polymer. When present, a dispersant polymer is typically at levels in the range from 0 wt-% to about 25 wt-%, preferably from about 0.5 wt-% to about 20 wt-%, more preferably from about 1 wt-% to about 8 wt-% of the detergent composition. Dispersant polymers are useful for improved filming performance of the present dishwasher detergent compositions, especially in higher pH embodiments, such as those in which wash pH exceeds about 9.5. Particularly preferred are polymers, which inhibit the deposition of calcium carbonate or magnesium silicate on dishware.

Suitable polymers are preferably at least partially neutralized or alkali metal, ammonium or substituted ammonium (e.g., mono-, di- or triethanolammonium) salts of polycarboxylic acids.

The alkali metal, especially sodium salts are most preferred. While the molecular weight of the polymer can vary over a wide range, it preferably is from about 1,000 to about 500,000, more preferably is from about 1,000 to about 250,000.

Unsaturated monomeric acids that can be polymerized to form suitable dispersant polymers include acrylic acid, maleic acid (or maleic anhydride), fumaric acid, itaconic acid, aconitic acid, mesaconic acid, citraconic acid and methylenemalonic acid. The presence of monomeric segments containing no carboxylate radicals such as methyl vinyl ether, styrene, ethylene, etc. is suitable provided that such segments do not constitute more than about 50 wt-% of the dispersant polymer.

Copolymers of acrylamide and acrylate having a molecular weight of from about 3,000 to about 100,000, preferably from about 4,000 to about 20,000, and an acrylamide content of less than about 50 wt-%, preferably less than about 20 wt-% of the dispersant polymer can also be used. Most preferably, such dispersant polymer has a molecular weight of from about 4,000 to about 20,000 and an acrylamide content of from about 0 wt-% to about 15 wt-%, based on the total weight of the polymer.

Particularly preferred dispersant polymers are low molecular weight modified polyacrylate copolymers. Such copolymers contain as monomer units: a) from about 90 wt-% to about 10 wt-%, preferably from about 80 wt-% to about 20 wt-% acrylic acid or its salts and b) from about 10 wt-% to about 90 wt-%, preferably from about 20 wt-% to about 80 wt-% of a substituted acrylic monomer or its salt and have the general formula:

$$-[(C(R_a)C(R_b)(C(O)OR_c)]$$

wherein the apparently unfilled valencies are in fact occupied by hydrogen and at least one of the substituents $R_a$, $R_b$, or $R_c$, preferably $R_a$ or $R_b$, is a 1 to 4 carbon alkyl or hydroxyalkyl group; $R_a$ or $R_b$ can be a hydrogen and $R_c$ can be a hydrogen or alkali metal salt. Most preferred is a substituted acrylic monomer wherein $R_a$ is methyl, $R_b$ is hydrogen, and $R_c$ is sodium.

A suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized form of the polymer comprising about 70 wt-% acrylic acid and about 30 wt-% methacrylic acid.

Other dispersant polymers useful herein include the polyethylene glycols and polypropylene glycols having a molecular weight of from about 950 to about 30,000.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other suitable dispersant polymers are the carboxylated polysaccharides, particularly starches, celluloses and alginates.

Yet another group of acceptable dispersants are the organic dispersant polymers, such as polyaspartate.

Depending on whether a greater or lesser degree of compactness is required, filler materials can also be present in the instant hard surface cleaning compositions, preferably dishwashing detergent formulations, more preferably automatic dishwashing detergent formulations. These include sucrose, sucrose esters, sodium sulfate, potassium sulfate, etc., in amounts up to about 70 wt-%, preferably from 0 wt-% to about 40 wt-% of the hard surface cleaning compositions, preferably dishwashing detergent formulations, more preferably automatic dishwashing detergent formulations. Preferred filler is sodium sulfate, especially in good grades having at most low levels of trace impurities.

Sodium sulfate used herein preferably has a purity sufficient to ensure it is non-reactive with bleach; it may also be treated with low levels of sequestrants, such as phosphonates or EDDS in magnesium-salt form. Note that preferences, in terms of purity sufficient to avoid decomposing bleach, applies also to pH-adjusting component ingredients, specifically including any silicates used herein.

Organic solvents that can be used in the cleaning formulations according to the invention, especially when the latter are in liquid or paste form, include alcohols having from 1 to 4 carbon atoms, especially methanol, ethanol, isopropanol and tert-butanol, diols having from 2 to 4 carbon atoms, especially ethylene glycol and propylene glycol, and mixtures thereof, and the ethers derivable from the mentioned classes of compound. Such water-miscible solvents are present in the cleaning formulations according to the invention preferably in amounts not exceeding 20 wt-%, especially in amounts of from 1 wt-% to 15 wt-%.

Many hard surface cleaning compositions, preferably dishwashing detergent formulations, more preferably automatic dishwashing detergent formulations herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH-jump systems, dual compartment containers, etc., and are well known to those skilled in the art. Certain hard surface cleaning compositions, preferably dishwashing detergent formulations, more preferably automatic dishwashing detergent formulations, comprise a pH-adjusting component selected from water-soluble alkaline inorganic salts and water-soluble organic or inorganic builders. The pH-adjusting components are selected so that when the hard surface cleaning composition, preferably dishwashing detergent formulation, more preferably automatic dishwashing detergent formulation is dissolved in water at a concentration of 1,000-5,000 ppm, the pH remains in the range of above about 8, preferably from about 9.5 to about 11. The preferred nonphosphate pH-adjusting component can be selected from the group consisting of:

(i) sodium carbonate or sesquicarbonate;
(ii) sodium silicate, preferably hydrous sodium silicate having $SiO_2$:$Na_2O$ ratio of from about 1:1 to about 2:1, and mixtures thereof with limited quantities of sodium metasilicate;
(iii) sodium citrate;
(iv) citric acid;
(v) sodium bicarbonate;
(vi) sodium borate, preferably borax;
(vii) sodium hydroxide; and
(viii) mixtures of (i)-(vii).

Preferred embodiments contain low levels of silicate (i.e. from about 3 wt-% to about 10 wt-% $SiO_2$).

Illustrative of highly preferred pH-adjusting component systems of this specialized type are binary mixtures of granular sodium citrate with anhydrous sodium carbonate, and three-component mixtures of granular sodium citrate trihydrate, citric acid monohydrate and anhydrous sodium carbonate.

The amount of the pH adjusting component in compositions used for automatic dishwashing is preferably from about 1 wt-% to about 50 wt-% of the composition. In a preferred embodiment, the pH-adjusting component is present in the composition in an amount from about 5 wt-% to about 40 wt-%, preferably from about 10 wt-% to about 30 wt-%.

For compositions herein having a pH between about 9.5 and about 11 of the initial wash solution, particularly preferred automatic dishwashing detergent formulations embodiments comprise, by weight of the automatic dishwashing detergent formulations, from about 5 wt-% to about 40 wt-%, preferably from about 10 wt-% to about 30 wt-%, most preferably from about 15 wt-% to about 20 wt-%, of sodium citrate with from about 5 wt-% to about 30 wt-%, preferably from about 7 wt-% to 25 wt-%, most preferably from about 8 wt-% to about 20 wt-% sodium carbonate.

The essential pH-adjusting system can be complemented (i.e. for improved sequestration in hard water) by other optional detergency builder salts selected from nonphosphate detergency builders known in the art, which include the various water-soluble, alkali metal, ammonium or substituted ammonium borates, hydroxysulfonates, polyacetates, and polycarboxylates. Preferred are the alkali metals, especially sodium, salts of such materials. Alternate water-soluble, non-phosphorus organic builders can be used for their sequestering properties. Examples of polyacetate and polycarboxylate builders are the sodium, potassium, lithium, ammonium and substituted ammonium salts of ethylenediamine tetraacetic acid; nitrilotriacetic acid, tartrate monosuccinic acid, tartrate disuccinic acid, oxydisuccinic acid, carboxymethoxysuccinic acid, mellitic acid, and sodium benzene polycarboxylate salts.

The detergent formulations can take a variety of physical forms such as, for example, powder granules, tablets (tabs), gel and liquid. Examples thereof include, inter alia, conventional high-performance detergent powders, supercompact high-performance detergent powders and tabs. One important physical form is the so-called concentrated granular form, which is added to a washing machine.

Also of importance are so-called compact or supercompact detergents. In the field of detergent manufacture, there is a trend towards the production of such detergents that contain an increased amount of active substances. In order to minimize energy consumption during the washing procedure, compact or supercompact detergents need to act effectively at low washing temperatures, for example below 40° C., or even at room temperature (25° C.). Such detergents usually contain only small amounts of fillers or of substances, such as sodium sulfate or sodium chloride, required for detergent manufacture. The total amount of such substances is usually from 0 to 10 wt-%, especially from 0 to 5 wt-%, more especially from 0 to 1 wt-%, based on the total weight of the detergent formulation. Such (super)compact detergents usually have a bulk density of from 650 to 1000 g/l, especially from 700 to 1000 g/l and more especially from 750 to 1000 g/l.

The detergent formulations can also be in the form of tablets (tabs). The advantages of tabs reside in the ease of dispensing and convenience in handling. Tabs are the most compact form of solid detergent formulation and usually have a volumetric density of, for example, from 0.9 to 1.3 kg/liter. To achieve rapid dissolution, such tabs generally contain special dissolution aids:
- carbonate/hydrogen carbonate/citric acid as effervescents;
- disintegrators, such as cellulose, carboxymethyl cellulose or cross-linked poly(N-vinylpyrrolidone);
- rapidly dissolving materials, such as sodium (potassium) acetates, or sodium (potassium) citrates;
- rapidly dissolving, water-soluble, rigid coating agents, such as dicarboxylic acids.

The tabs may also comprise combinations of such dissolution aids.

The detergent formulation may also be in the form of an aqueous liquid containing from 5 wt-% to 50 wt-%, preferably from 10 wt-% to 35 wt-%, of water or in the form of a non-aqueous liquid containing no more than 5 wt-%, preferably from 0 wt-% to 1 wt-% of water. Non-aqueous liquid detergent formulations may comprise other solvents as carriers. Low molecular weight primary or secondary alcohols, for example methanol, ethanol, propanol and isopropanol, are suitable for that purpose. The solubilising surfactant used is preferably a monohydroxy alcohol but polyols, such as those containing from 2 to 6 carbon atoms and from 2 to 6 hydroxy groups (e.g., 1,3-propanediol, ethylene glycol, glycerol and 1,2-propanediol) can also be used. Such carriers are usually used in a total amount of from 5 wt-% to 90 wt-%, preferably from 10 wt-% to 50 wt-%, based on the total weight of the detergent formulation. The detergent formulations can also used in so-called "unit liquid dose" form.

Also an aspect of the invention is a granule comprising
a) from 1-99 wt-%, based on the total weight of the granule, of at least one metal complex compound of formula (1) or a ligand of formula (2) as defined above and of at least one peroxide,
b) from 1-99 wt-%, based on the total weight of the granule, of at least one binder,
c) from 0-20 wt-%, based on the total weight of the granule, of at least one encapsulating material,
d) from 0-20 wt-%, based on the total weight of the granule, of at least one further additive and
e) from 0-20 wt-% based on the total weight of the granule, of water.

All wt-% are based on the total weight of the granule.

As binder (b) there come into consideration water-soluble, dispersible or water-emulsifiable anionic dispersants, non-ionic dispersants, polymers and waxes.

The anionic dispersants used are, for example, commercially available water-soluble anionic dispersants for dyes, pigments etc.

The following products, especially, come into consideration: condensation products of aromatic sulfonic acids and formaldehyde, condensation products of aromatic sulfonic acids with unsubstituted or chlorinated diphenyls or diphenyl oxides and optionally formaldehyde, (mono-/di-)alkylnaphthalenesulfonates, sodium salts of polymerised organic sulfonic acids, sodium salts of polymerised alkylnaphthalenesulfonic acids, sodium salts of polymerised alkylbenzenesulfonic acids, alkylarylsulfonates, sodium salts of alkyl polyglycol ether sulfates, polyalkylated polynuclear arylsulfonates, methylene-linked condensation products of arylsulfonic acids and hydroxyarylsulfonic acids, sodium salts of dialkylsulfosuccinic acid, sodium salts of alkyl diglycol ether sulfates, sodium salts of polynaphthalenemethanesulfonates, lignosulfonates or oxylignosulfonates and heterocyclic polysulfonic acids.

Especially suitable anionic dispersants are condensation products of naphthalenesulfonic acids with formaldehyde, sodium salts of polymerised organic sulfonic acids, (mono-/di-)-alkylnaphthalenesulfonates, polyalkylated polynuclear arylsulfonates, sodium salts of polymerised alkylbenzenesulfonic acid, lignosulfonates, oxylignosulfonates and condensation products of naphthalenesulfonic acid with a polychloromethyldiphenyl.

Suitable non-ionic dispersants are especially compounds having a melting point of, preferably, at least 35° C. that are emulsifiable, dispersible or soluble in water, for example the following compounds:
1. fatty alcohols having from 8 to 22 carbon atoms, especially cetyl alcohol;
2. addition products of, preferably, from 2 to 80 mol of alkylene oxide, especially ethylene oxide, wherein some of the ethylene oxide units may have been replaced by substituted epoxides, such as styrene oxide and/or propylene oxide, with higher unsaturated or saturated monoalcohols, fatty acids, fatty amines or fatty amides having from 8 to 22 carbon atoms or with benzyl alcohols, phenyl phenols, benzyl phenols or alkyl phenols, the alkyl radicals of which have at least 4 carbon atoms;
3. alkylene oxide, especially propylene oxide, condensation products (block polymers);
4. ethylene oxide/propylene oxide adducts with diamines, especially ethylenediamine;
5. reaction products of a fatty acid having from 8 to 22 carbon atoms and a primary or secondary amine having at least one hydroxy-lower alkyl or lower alkoxy-lower alkyl group, or alkylene oxide addition products of such hydroxyalkyl-group-containing reaction products;
6. sorbitan esters, preferably having long-chain ester groups, or ethoxylated sorbitan esters, such as polyoxyethylene sorbitan monolaurate having from 4 to 10 ethylene oxide units or polyoxyethylene sorbitan trioleate having from 4 to 20 ethylene oxide units;
7. addition products of propylene oxide with a tri- to hexahydric aliphatic alcohol having from 3 to 6 carbon atoms, e.g. glycerol or pentaerythritol; and
8. fatty alcohol polyglycol mixed ethers, especially addition products of from 3 to 30 mol of ethylene oxide and from 3 to 30 mol of propylene oxide with aliphatic monoalcohols having from 8 to 22 carbon atoms.

Especially suitable non-ionic dispersants are surfactants of formula

   (11), wherein $R_{23}$ is $C_8$-$C_{22}$alkyl or $C_8$-$C_{18}$alkenyl;

$R_{24}$ is hydrogen; $C_1$-$C_4$alkyl; a cycloaliphatic radical having at least 6 carbon atoms; or benzyl;

"alkylene" is an alkylene radical having from 2 to 4 carbon atoms and n is a number from 1 to 60.

The substituents $R_{23}$ and $R_{24}$ in formula (11) are advantageously each the hydrocarbon radical of an unsaturated or, preferably, saturated aliphatic monoalcohol having from 8 to 22 carbon atoms. The hydrocarbon radical may be straight-chain or branched. $R_{23}$ and $R_{24}$ are preferably each independently of the other an alkyl radical having from 9 to 14 carbon atoms.

Aliphatic saturated monoalcohols that come into consideration include natural alcohols, e.g. lauryl alcohol, myristyl alcohol, cetyl alcohol or stearyl alcohol, and also synthetic alcohols, e.g. 2-ethylhexanol, 1,1,3,3-tetramethylbutanol, octan-2-ol, isononyl alcohol, trimethylhexanol, trimethylnonyl alcohol, decanol, $C_9$-$C_{11}$oxo-alcohol, tridecyl alcohol, isotridecyl alcohol and linear primary alcohols (Alfols) having from 8 to 22 carbon atoms. Some examples of such Alfols are Alfol (8-10), Alfol (9-11), Alfol (10-14), Alfol (12-13) and Alfol (16-18). ("Alfol" is a registered trade mark of the company Sasol Limited).

Unsaturated aliphatic monoalcohols are, for example, dodecenyl alcohol, hexadecenyl alcohol and oleyl alcohol.

The alcohol radicals may be present singly or in the form of mixtures of two or more components, e.g. mixtures of alkyl and/or alkenyl groups that are derived from soybean fatty acids, palm kernel fatty acids or tallow oils.

(Alkylene-O) chains are preferably bivalent radicals of the formulae

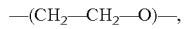,

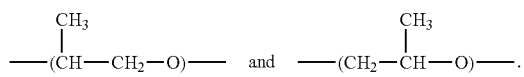

Examples of a cycloaliphatic radical include cycloheptyl, cyclooctyl and preferably cyclohexyl.

As non-ionic dispersants there come into consideration preferably surfactants of formula

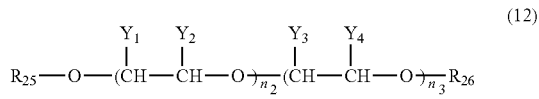   (12)

wherein $R_{25}$ is $C_8$-$C_{22}$alkyl;

$R_{26}$ is hydrogen or $C_1$-$C_4$alkyl;

$Y_1, Y_2, Y_3$ and $Y_4$ are each independently of the others hydrogen, methyl or ethyl;

$n_2$ is a number from 0 to 8; and $n_3$ is a number from 2 to 40.

Further important non-ionic dispersants correspond to formula

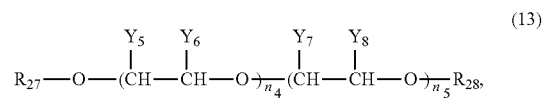   (13)

wherein $R_{27}$ is $C_9$-$C_{14}$alkyl;

$R_{28}$ is $C_1$-$C_4$alkyl;

$Y_5, Y_6, Y_7$ and $Y_8$ are each independently of the others hydrogen, methyl or ethyl, one of the radicals $Y_5, Y_6$ and one of the radicals $Y_7, Y_8$ always being hydrogen; and $n_4$ and $n_5$ are each independently of the other an integer from 4 to 8.

The non-ionic dispersants of formulae (11) to (13) can be used in the form of mixtures. For example, as surfactant mixtures there come into consideration non-end-group-terminated fatty alcohol ethoxylates of formula (7), e.g. compounds of formula (11) wherein $R_{23}$ is $C_8$-$C_{22}$alkyl, $R_{24}$ is hydrogen and the alkylene-O chain is the radical —($CH_2$—$CH_2$—O)— and also end-group-terminated fatty alcohol ethoxylates of formula (9).

Examples of non-ionic dispersants of formulae (11), (12) and (13) include reaction products of a $C_{10}$-$C_{13}$ fatty alcohol, e.g. a $C_{13}$oxo-alcohol, with from 3 to 10 mol of ethylene oxide, propylene oxide and/or butylene oxide and the reaction product of one mol of a $C_{13}$ fatty alcohol with 6 mol of ethylene oxide and 1 mol of butylene oxide, it being possible for the addition products each to be end-group-terminated with $C_1$-$C_4$alkyl, preferably methyl or butyl.

Such dispersants can be used singly or in the form of mixtures of two or more dispersants. Instead of, or in addition to, the anionic or non-ionic dispersant, the granules according to the invention may comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain α-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyltrimethylammonium chloride, terpolymers of caprolactam/vinylpyrrolidone/dimethylaminoethyl methacrylates, copolymers of styrene and acrylic acid, polycarboxylic acids, polyacrylamides, carboxymethyl cellulose, hydroxymethyl cellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxymethyl cellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolymers of ethyl acrylate with methacrylate and methacrylic acid, and polymathacrylates.

Suitable water-emulsifiable or water-dispersible binders also include paraffin waxes.

Encapsulating materials (c) include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents.

The preparation of the granules according to the invention is carried out, for example, starting from:

a) a solution or suspension with a subsequent drying/shaping step or b) a suspension of the active ingredient in a melt with subsequent shaping and solidification.

a) First of all the anionic or non-ionic dispersant and/or the polymer and, optionally, the further additives are dissolved in water and stirred, if desired with heating, until a homogeneous solution is obtained. The catalyst according to the invention is then dissolved or suspended in the resulting aqueous solution. The solids content of the solution should preferably be at least 30 wt-%, especially from 40 wt-% to 50 wt-%, based on the total weight of the solution. The viscosity of the solution is preferably less than 200 mPas.

The aqueous solution so prepared, comprising the catalyst according to the invention, is then subjected to a drying step in which all water, with the exception of a residual amount, is removed, solid particles (granules) being formed at the same time. Known methods are suitable for producing the granules from the aqueous solution. In principle, both continuous methods and discontinuous methods are suitable. Continuous methods are preferred, especially spray-drying and fluidised bed granulation processes.

Especially suitable are spray-drying processes in which the active ingredient solution is sprayed into a chamber with circulating hot air. The atomisation of the solution is effected e.g. using unitary or binary nozzles or is brought about by the spinning effect of a rapidly rotating disc. In order to increase the particle size, the spray-drying process may be combined with an additional agglomeration of the liquid particles with solid nuclei in a fluidised bed that forms an integral part of the chamber (so-called fluid spray). The fine particles (<100 μm) obtained by a conventional spray-drying process may, if necessary after being separated from the exhaust gas flow, be fed as nuclei, without further treatment, directly into the atomizing cone of the atomiser of the spray-dryer for the purpose of agglomeration with the liquid droplets of the active ingredient.

During the granulation step, the water can rapidly be removed from the solutions comprising the catalyst according to the invention, binder and further additives. It is expressly intended that agglomeration of the droplets forming in the atomising cone, or agglomeration of droplets with solid particles, will take place.

b) The catalyst according to the invention is dried in a separate step prior to the melt-granulation and, if necessary, dry-ground in a mill so that all the solids particles are <50 μm in size. The drying is carried out in an apparatus customary for the purpose, for example, in a paddle dryer, vacuum cabinet or freeze-dryer.

Other product forms of the present invention include product forms specifically developed for industrial and institutional cleaning, for example liquid solutions of the catalyst in water or organic solvents or solid forms such as powders or granules which can be dosed in a separate bleaching step of the cleaning application.

Some of the ligands defined above are novel and are also a subject of the present invention.

A compound of formula (2)

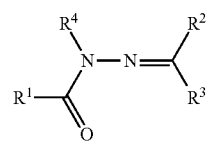

(2)

wherein $R_1$ is $-(CH_2)_k-N^+(R_{100}R'_{100}R''_{100})_3A^-$, wherein $A^-$ is an anion and k is a number from 1 to 4; or phenyl substituted with 1 to 5 electron withdrawing substituents $-N(R_{100}R'_{100}R''_{100})_3{}^+A^-$ wherein the $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; and $A^-$ is an anion, or $R_1$ together with the electron withdrawing substituent is a group

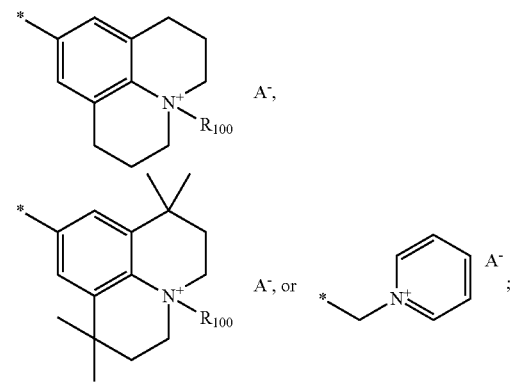

* is the point of attachment;

$R_4$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl;

$R_2$ and $R_3$ independently of each other denote hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl; or $R_2$ and $R_3$, together with the alkylidene carbon atom linking them, form an unsubstituted or substituted ring 5-, 6-, 7-, 8- or 9-membered ring which may contain further hetero atoms.

Preferred is a compound of formula (2)

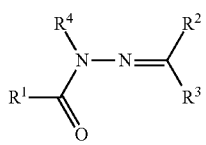
(2)

wherein
$R_1$ is phenyl substituted with 1 to 5 electron withdrawing substituents —$N(R_{100}R'_{100}R''_{100})_3{}^+A^-$ wherein the $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; and $A^-$ is an anion, or
$R_1$ together with the electron withdrawing substituent is a group

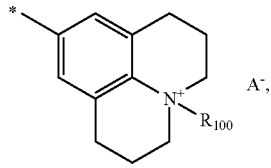

* is the point of attachment;
$R_4$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl;
$R_2$ and $R_3$ independently of each other denote hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl; or
$R_2$ and $R_3$, together with the alkylidene carbon atom linking them, form an unsubstituted or substituted ring 5-, 6-, 7-, 8- or 9-membered ring which may contain further hetero atoms.

For example a compound which is of formula (5)

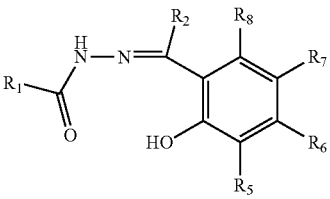
(5)

wherein
$R_1$ is phenyl substituted with 1 to 5 electron withdrawing substituents —$N(R_{100}R'_{100}R''_{100})_3{}^+A^-$ wherein the $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; and $A^-$ is an anion, or
$R_1$ together with the electron withdrawing substituent is a group

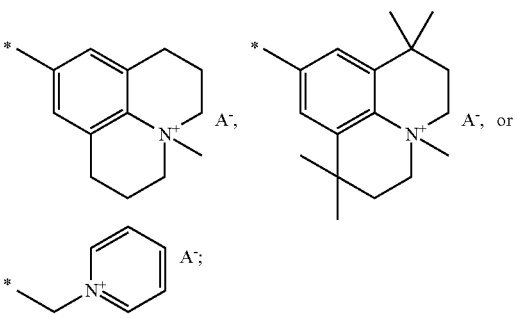

* is the point of attachment;
$R_2$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted aryl, or unsubstituted or substituted heteroaryl;
$R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl; —$OR_{100}$, —$NR_{100}R'_{100}$, halogen or a group

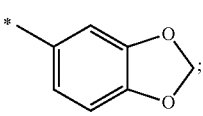

or independently have the meaning as defined for $R_1$;
or
$R_5$ and $R_6$, $R_6$ and $R_7$ or $R_7$ and $R_8$, are linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups.

Preferred is a compound wherein $R_1$ is phenyl substituted with 1 to 5 electron withdrawing substituents —$N(R_{100}R'_{100}R''_{100})_3{}^+A^-$ wherein the $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; and $A^-$ is $F^-$, $Cl^-$, $Br^-$ or $I^-$, or $R_1$ together with the electron withdrawing substituent is a group

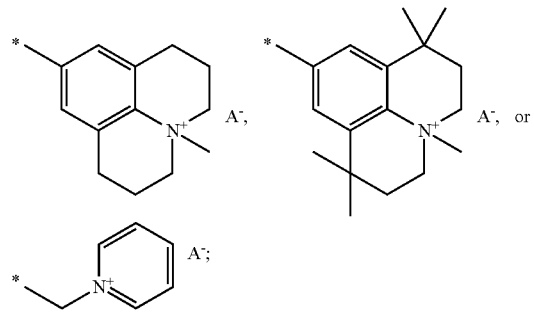

* is the point of attachment;

$R_2$ denotes hydrogen, unsubstituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$-phenylalkyl, $C_3$-$C_{20}$heteroalkyl, $C_3$-$C_{12}$cycloheteroalkyl halogen;

$R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl;

or —$OR_{100}$, —$NHR_{100}$, —$NR_{100}R'_{100}$, halogen;

or phenyl substituted with 1 to 5 electron withdrawing groups selected from the group consisting of —$OR(O)OR_{100}$, —$COOR_{100}$, —$C(O)$—$R_{100}$, —$CN$, —$NO_2$, —$SO_3R_{100}$, —$CF_3$, F, Cl, Br, I, —$OR_{100}$, —$N(R_{100}R'_{100}R''_{100})_3{}^+A^-$ and

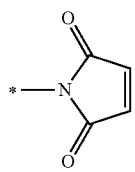

wherein $R_{100}$, $R'_{100}$, $R''_{100}$ independently are hydrogen, $C_1$-$C_{18}$alkyl or phenyl, * is the point of attachment and $A^-$ is as defined above; or $R_5$, $R_6$, $R_7$ and $R_8$ together with the electron withdrawing substituent are independently a group

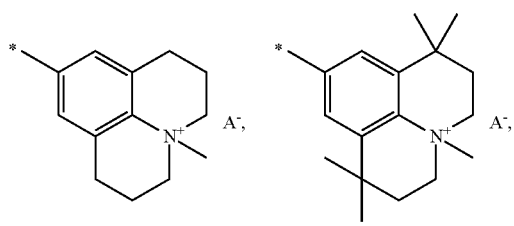

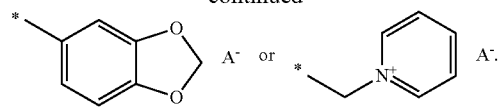

Preferably $R_1$ is phenyl substituted with 1 to 3 electron withdrawing substituents —$N(R_{100})_3{}^+A^-$, more preferably with 1 or 2 and most preferably with 1.

Yet a further aspect of the invention is a complex compound of formula (3a) or (4a)

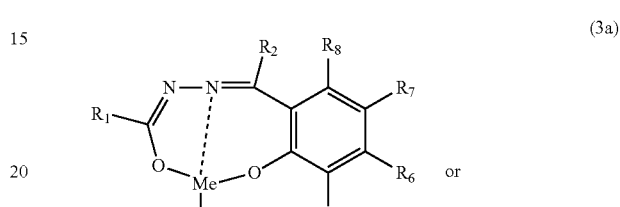

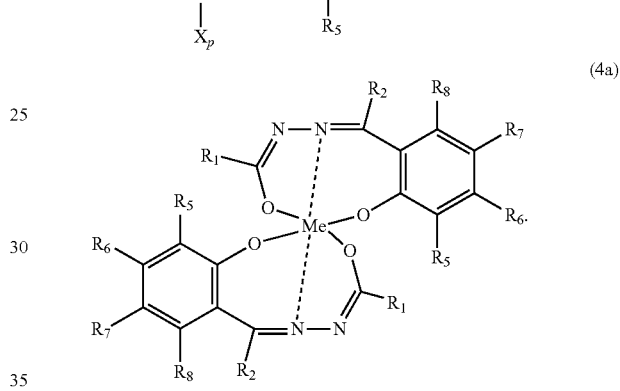

wherein

Me is manganese in oxidation states II-V or iron in oxidation states I to IV;

X is $CH_3CN$, $H_2O$, $F^-$, $Cl^-$, $Br^-$, $HOO^-$, $O_2{}^{2-}$, $O^{2-}$, $R_{28}COO^-$, $R_{28}O^-$;

$R_{28}$ is hydrogen, unsubstituted or substituted $C_1$-$C_{18}$alkyl or phenyl;

p is an integer from 1 to 4;

$R_1$ is —$(CH_2)_k$—$N^+(R_{100}R'_{100}R''_{100})_3 A^-$, wherein $A^-$ is an anion and k is a number from 1 to 4; or phenyl substituted with 1 to 5 electron withdrawing substituents —$N(R_{100}R'_{100}R''_{100})_3{}^+A^-$ wherein the $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; and $A^-$ is $F^-$, $Cl^-$, $Br^-$ or I, or $R_1$ together with the electron withdrawing substituent is a group

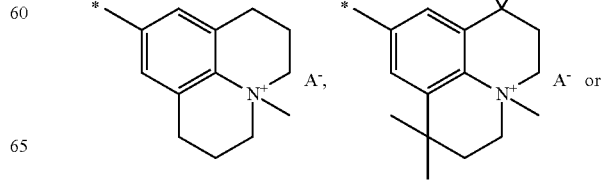

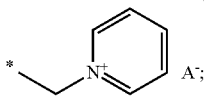

* is the point of attachment;
$R_2$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted aryl, or unsubstituted or substituted heteroaryl;
$R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl; —$OR_{100}$, —$NR_{100}R'_{100}$, halogen or a group

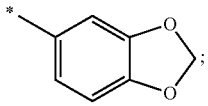

or independently have the meaning as defined for $R_1$;
or
$R_5$ and $R_6$, $R_6$ and $R_7$ or $R_7$ and $R_8$, are linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups.
Yet a further aspect of the invention is a complex compound of formula (3a) or (4a)

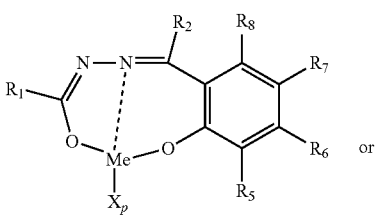

(3a)

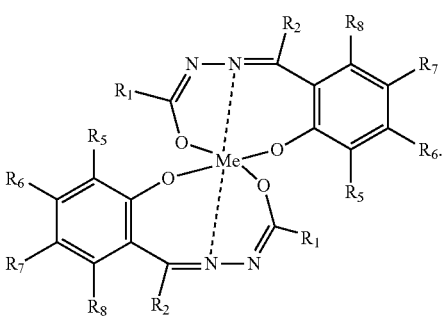

(4a)

wherein
Me is manganese in oxidation states II-V or iron in oxidation states I to IV;
X is $CH_3CN$, $H_2O$, $F^-$, $Cl^-$, $Br^-$, $HOO^-$, $O_2^{2-}$, $O^{2-}$, $R_{28}COO^-$, $R_{28}O^-$;

$R_{28}$ is hydrogen, unsubstituted or substituted $C_1$-$C_{18}$alkyl or phenyl;
p is an integer from 1 to 4;
$R_1$ is phenyl substituted with 1 to 5 electron withdrawing substituents —$N(R_{100}R'_{100}R''_{100})_3^+A^-$ wherein the $R_{100}$, $R'_{100}$, $R''_{100}$ independently are hydrogen, $C_1$-$C_{18}$alkyl or phenyl, or two of $R_{100}$, $R'_{100}$, $R''_{100}$ together with the nitrogen atom to which they are bonded form a 5 or 6 membered-ring which may contain a further nitrogen atom; and $A^-$ is $F^-$, $Cl^-$, $Br^-$ or $I^-$, or
$R_1$ together with the electron withdrawing substituent is a group

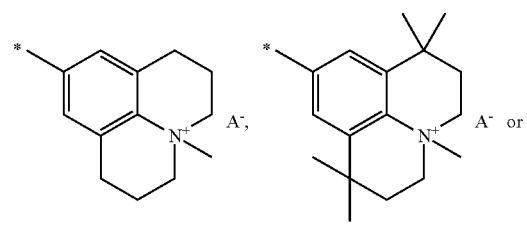

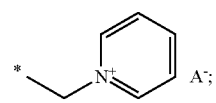
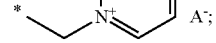

* is the point of attachment;
$R_2$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted aryl, or unsubstituted or substituted heteroaryl;
$R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl; —$OR_{100}$, —$NR_{100}R'_{100}$, halogen or a group

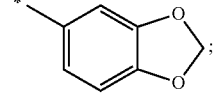

or independently have the meaning as defined for $R_1$;
or
$R_5$ and $R_6$, $R_6$ and $R_7$ or $R_7$ and $R_8$, are linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups.
All definitions and preferences given above apply where applicable equally to all aspects of the invention.
The following examples illustrate the invention.

SYNTHESIS EXAMPLE 1

Preparation of

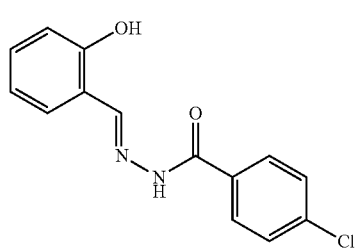

E/Z isomers and tautomeric forms

A mixture of 3.48 g of 4-chlorobenzhydrazide and 2.47 g of salicylaldehyde in 80 mL of ethanol is heated to 50° C. After stirring for 30 minutes at this temperature 1 mL of concentrated hydrochloric acid is added. The resulting pale yellow suspension is stirred for 16 hours, then filtrated and the residue washed with minor amounts of ethanol. After drying at 60° C. in the vacuum 4.18 g of the desired product as a pale beige powder is obtained. Melting point: 223° C.

SYNTHESIS EXAMPLE 2

Preparation of

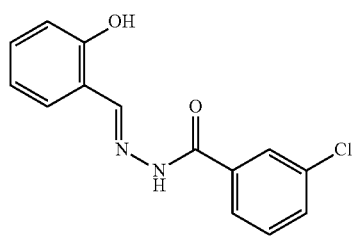

E/Z isomers and tautomeric forms 1.15 g of 3-chlorobenzhydrazide are suspended in 35 mL of ethanol and stirred at room temperature for 10 minutes. After addition of 0.93 g of salicylaldehyde and 1 mL of concentrated hydrochloric acid the resulting yellow solution is stirred for 16 hours at room temperature. A colorless precipitate is filtrated off, washed with 10 mL of water and dried at 100° C. in the vacuum yielding 1.39 g of the desired product as a colorless powder. Melting point: 201.8° C.

SYNTHESIS EXAMPLE 3

Preparation of

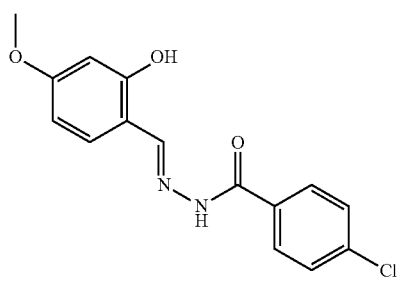

E/Z isomers and tautomeric forms

To a mixture of 0.44 g of 4-chlorobenzhydrazide and 0.39 g of 2-hydroxy-4-methoxy-benzaldehyde in 35 mL of ethanol is added 0.5 mL of concentrated hydrochloric acid. Immediately a yellow suspension is formed which is stirred at room temperature for 16 hours. After filtrating off a pale yellow powder which is washed with 5 mL of ethanol and dried at 70° C. in vacuum 0.60 g of the desired product are obtained. Melting point: 196.9° C.

SYNTHESIS EXAMPLE 4

Preparation of

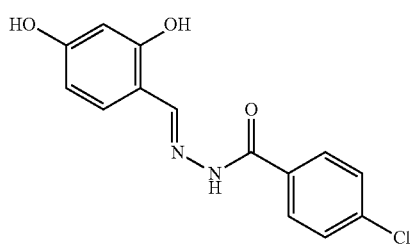

E/Z isomers and tautomeric forms

To a mixture of 0.44 g of 4-chlorobenzhydrazide and 0.39 g of 2,4-dihydroxy-benzaldehyde in 35 mL of ethanol is added 0.5 mL of concentrated hydrochloric acid. Immediately a reddish brown solution is formed which is stirred at room temperature for 16 hours. After filtrating off a beige powder which is washed with 5 mL of water and dried at 70° C. in vacuum 0.17 g of the desired product are obtained. Melting point: 280° C.

SYNTHESIS EXAMPLE 5

Preparation of

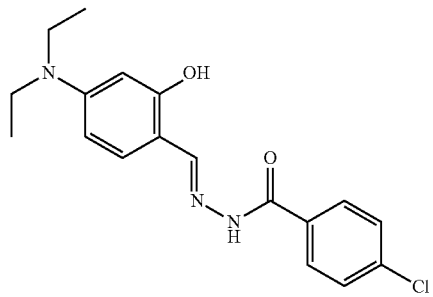

L5

E/Z isomers and tautomeric forms

To a mixture of 0.44 g of 4-chlorobenzhydrazide in 35 mL of ethanol 0.49 g of 4-diethylamino-2-hydroxy-benzaldehyde is added dropwise. After the addition of 0.5 mL of concentrated hydrochloric acid a brown solution is formed which is stirred at room temperature for 16 hours. A brownish precipitate is filtered off, washed with 5 mL of water and dried at 70° C. in vacuum yielding 0.70 g of the desired product are obtained. Melting point: 210° C.

SYNTHESIS EXAMPLE 6

Preparation of

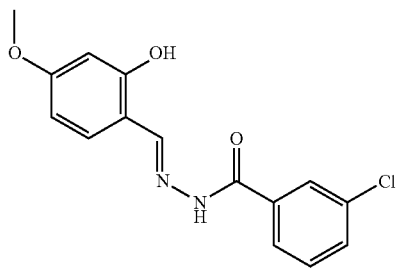

L6

E/Z isomers and tautomeric forms

To a mixture of 0.44 g of 3-chlorobenzhydrazide in 35 mL of ethanol 0.39 g of 2-hydroxy-4-methoxy-benzaldehyde is added dropwise. After addition of 0.5 mL of concentrated hydrochloric acid a yellow solution is formed which is stirred at room temperature for 16 hours. A pale yellow precipitate is then filtered off, which is washed with 5 mL of water and dried at 70° C. in vacuum yielding 0.38 g of the desired product. Melting point: 181.3° C.

SYNTHESIS EXAMPLE 7

Preparation of

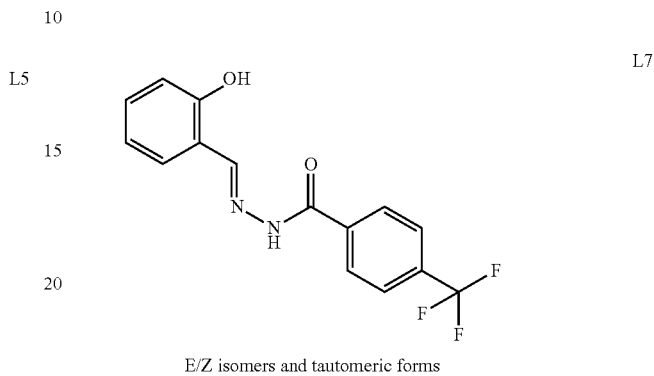

L7

E/Z isomers and tautomeric forms

To a mixture of 0.52 g of 4-trifluoromethyl-benzhydrazide in 15 mL ethanol 0.31 g of salicyl aldehyde is added dropwise at room temperature. Immediately a colorless suspension is formed. After addition of 0.5 mL of concentrated hydrochloric acid the suspension is stirred for 16 hours at room temperature. The precipitate is then filtrated off, washed with 5 mL of ethanol and dried in the vacuum at 50° C. yielding 0.20 g of the desired product as a colorless powder. Melting point: 230.6° C.

SYNTHESIS EXAMPLE 8

Preparation of

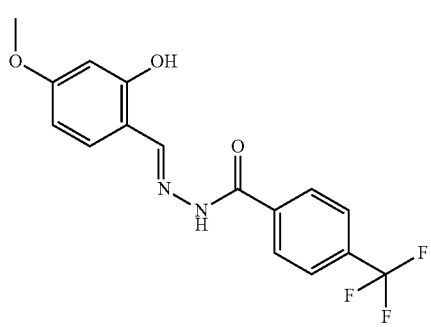

L8

E/Z isomers and tautomeric forms

To a mixture of 0.52 g of 4-trifluoromethyl-benzhydrazide in 15 mL ethanol 0.39 g of 2-hydroxy-4-methoxy-benzaldehyde is added dropwise at room temperature. After addition of 0.5 mL of concentrated hydrochloric acid a yellow suspension is formed which is stirred for 16 hours at room temperature. The precipitate is then filtrated off, washed with 5 mL of ethanol and dried in the vacuum at 50° C. yielding 0.51 g of the desired product as a yellow powder. Melting point: 200° C. (under decomposition).

SYNTHESIS EXAMPLE 9

Preparation of

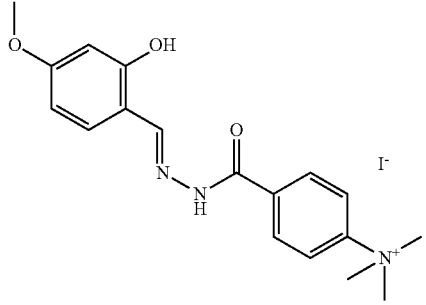

L9

E/Z isomers and tautomeric forms

To a mixture of 0.39 g of (4-hydrazinocarbonyl-phenyl)-trimethyl-ammonium iodide in 35 mL of ethanol 0.19 g of 2-hydroxy-4-methoxy-benzaldehyde is added dropwise at room temperature under formation of a colorless suspension. After addition of 0.5 mL of concentrated hydrochloric acid a yellow suspension is formed which is stirred for 16 hours at room temperature. The precipitate is then filtrated off, washed with 5 mL of water and dried in the vacuum at 70° C. yielding 0.17 g of the desired product as a colorless powder. Melting point: 176.8° C.

SYNTHESIS EXAMPLE 10

Preparation of

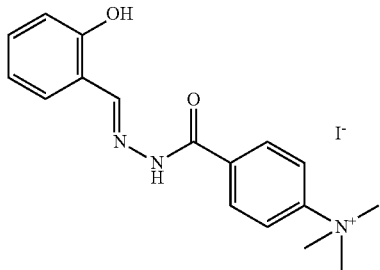

L10

E/Z isomers and tautomeric forms

To a mixture of 0.39 g of (4-hydrazinocarbonyl-phenyl)-trimethyl-ammonium iodide in 35 mL of ethanol 0.15 g of salicylaldehyde is added dropwise at room temperature under formation of a colorless suspension. After addition of 0.5 mL of concentrated hydrochloric acid stirring is continued for 16 hours at room temperature. A colorless precipitate is then filtrated off and dried in the vacuum at 70° C. yielding 0.21 g of the desired product as a colorless powder. Melting point: 170.4° C.

SYNTHESIS EXAMPLE 11

Preparation of

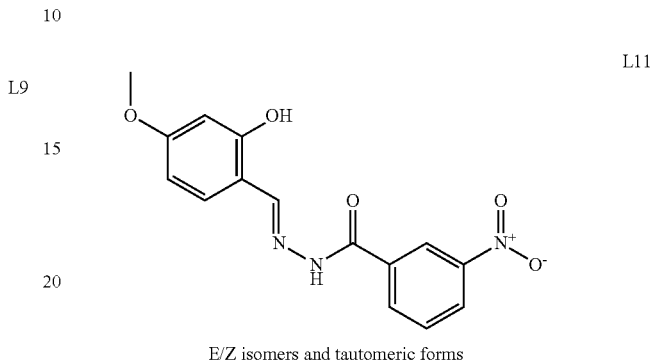

L11

E/Z isomers and tautomeric forms 0.46 g of 3-nitrobenzhydrazide are stirred for 10 min. in 35 mL of ethanol. Then 0.39 g of 2-hydroxy-4-methoxy-benzaldehyde are added dropwise at room temperature. After addition of 0.5 mL of concentrated hydrochloric acid immediately a precipitate is formed. The yellow suspension is stirred for 16 hours at room temperature. The precipitate is then filtrated off, washed with 5 mL of water and dried in the vacuum at 100° C. yielding 0.68 g of the desired product as a yellow solid. Melting point: 253.7° C.

SYNTHESIS EXAMPLE 12

Preparation of

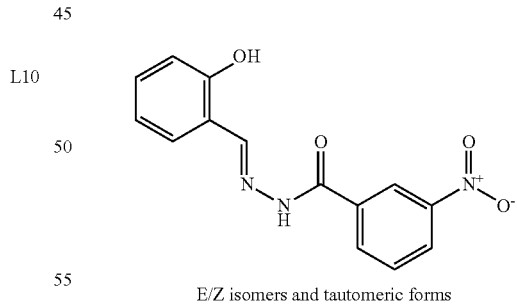

L12

E/Z isomers and tautomeric forms 1.39 g of 3-nitrobenzhydrazide are stirred for 30 min. in 35 mL of ethanol. Then 0.93 g of salicyl aldehyde are added dropwise at room temperature. After addition of 1 mL of concentrated hydrochloric acid a yellow suspension is formed. The yellow suspension is stirred for 16 hours at room temperature. The precipitate is then filtrated off, washed with 10 mL of water and dried in the vacuum at 100° C. yielding 2.00 g of the desired product as a yellowish powder. Melting point: 243.7° C.

SYNTHESIS EXAMPLE 13

Preparation of

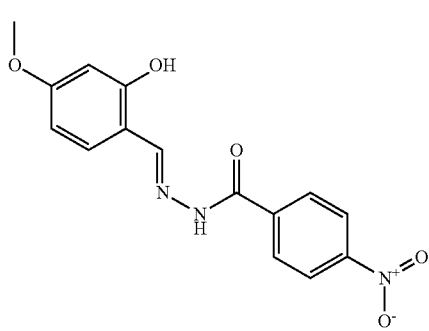

L13

E/Z isomers and tautomeric forms 0.46 g of 4-nitrobenzhydrazide are stirred for 10 minutes in 35 mL of ethanol resulting in a yellowish suspension. Then 0.39 g of 2-hydroxy-4-methoxy-benzaldehyde are added dropwise at room temperature. After addition of 0.5 mL of concentrated hydrochloric acid the yellow suspension is stirred for 16 hours at room temperature. The precipitate is then filtrated off, washed with 5 mL of water and dried in the vacuum at 100° C. yielding 0.70 g of the desired product as a dark yellow powder. Melting point: 214.8° C.

SYNTHESIS EXAMPLE 14

Preparation of

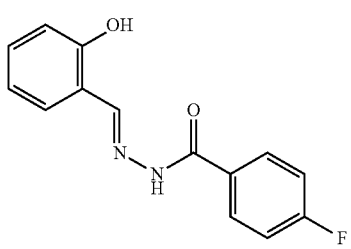

L14

E/Z isomers and tautomeric forms

A mixture of 1.21 g of 4-fluorobenzhydrazide and 0.95 g of salicylaldehyde in 40 mL of ethanol is heated to 60° C. After addition of 5 drops of concentrated acetic acid the mixture is stirred for 1 hour at refluxing temperature. After cooling down to room temperature a colorless precipitate is filtered off and dried at 60° C. in the vacuum yielding 0.97 g of the desired product as a colorless powder.

SYNTHESIS EXAMPLE 15

Preparation of

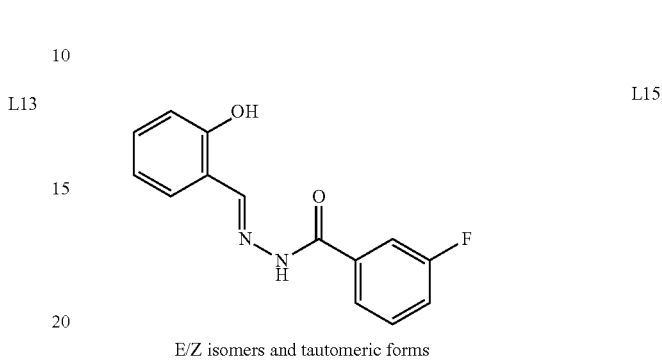

L15

E/Z isomers and tautomeric forms 0.99 g of 3-fluorobenzhydrazide are dissolved in 30 mL of ethanol by stirring and heating. After addition of 0.78 g of salicylaldehyde and 5 drops of concentrated acetic acid the resulting yellowish solution is stirred for 1 hour at refluxing temperature. A colorless precipitate is filtrated off, washed with water and dried at 60° C. in the vacuum yielding 1.01 g of the desired product as a colorless powder.

SYNTHESIS EXAMPLE 16

Preparation of

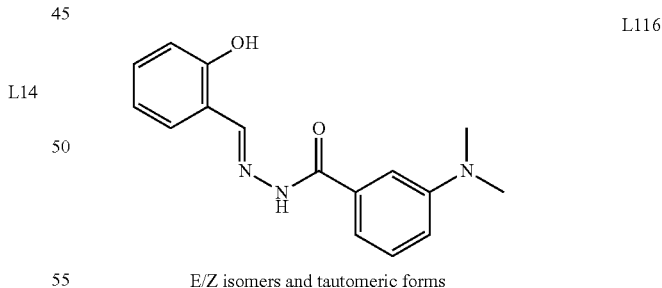

L116

E/Z isomers and tautomeric forms 330 mg of 3-dimethylbenzhydrazide are dissolved in 6 mL of ethanol by stirring. After addition of 225 mg of salicylaldehyde and 0.5 mL of concentrated hydrochloric acid the resulting yellowish suspension is stirred for 4 hours at room temperature. The precipitate is then filtrated off and recrys-

SYNTHESIS EXAMPLE 17

Preparation of

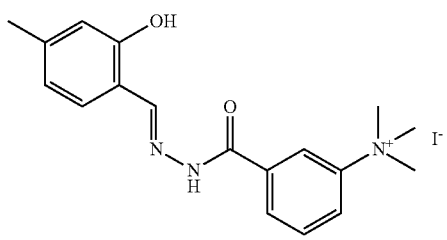

L117

E/Z isomers and tautomeric forms 134 mg of (3-hydrazinocarbonyl-phenyl)-trimethyl-ammonium iodide are stirred for 10 minutes in 8 mL of ethanol. Then 315 mg of 2-hydroxy-4-methyl-benzaldehyde are added at room temperature. After addition of 0.5 mL of concentrated hydrochloric acid the resulting yellowish suspension is stirred for 0.5 hours at room temperature. The precipitate is then filtrated off and dried in the vacuum at 25° C., yielding 285 mg of the desired product as a yellow powder. Melting point: 185.7° C.

SYNTHESIS EXAMPLE 18

Preparation of

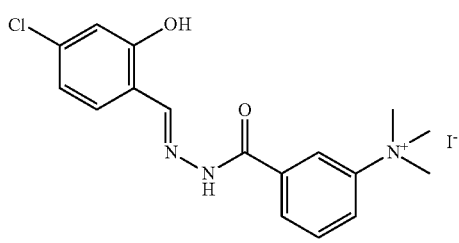

L118

E/Z isomers and tautomeric forms

To a mixture of 248 mg of (3-hydrazinocarbonyl-phenyl)-trimethyl-ammonium iodide in 7.5 mL of ethanol 121 mg of 4-chloro-2-hydroxybenzaldehyde are added at room temperature under formation of a colorless suspension. After addition of 0.5 mL of concentrated hydrochloric acid stirring is continued for 16 hours at room temperature. A yellow precipitate is then filtrated off and recrystallised from ethanol. After drying in the vacuum at 25° C., 98 mg of the desired product are isolated as a yellow powder. Melting point: 192.6° C.

SYNTHESIS EXAMPLE 19

Preparation of

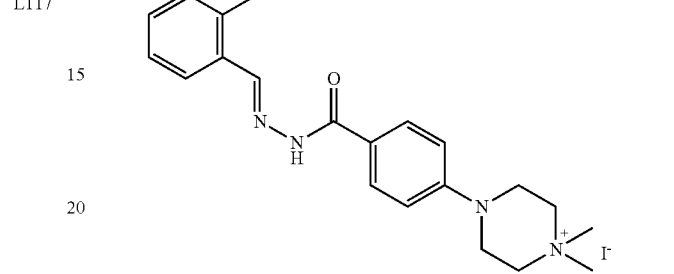

L119

E/Z isomers and tautomeric forms 61 mg of 4-(4-hydrazinocarbonyl-phenyl)-1,1-dimethyl-piperazin-1-ium iodide are stirred for 10 minutes in 5 mL of ethanol. Then 20 mg of salicylaldehyde are added at room temperature. After addition of 0.5 mL concentrated hydrochloric acid the resulting orange suspension is stirred for 16 hours at room temperature. The precipitate is then filtrated off and dried in the vacuum at 25° C., yielding 26 mg of the desired product as an orange powder.

SYNTHESIS EXAMPLE 20

Preparation of

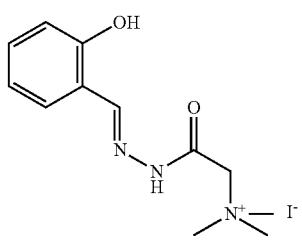

L120

E/Z isomers and tautomeric forms 250 mg of hydrazinocarbonylmethyl-trimethyl-ammonium iodide are suspended in 2.5 mL of ethanol by stirring. After addition of 118 mg of salicylaldehyde and 0.25 mL of concentrated hydrochloric acid the resulting yellowish suspension is stirred for 16 hours at room temperature. The precipitate is then filtrated off and washed with ethanol. After drying in the vacuum at 25° C., 270 mg of the desired product are isolated as a yellow powder.

SYNTHESIS EXAMPLE 21

Preparation of

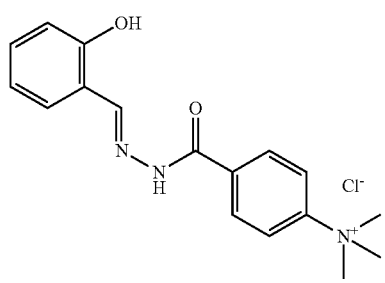
L121

E/Z isomers and tautomeric forms

To a solution of 0.755 g of (4-hydrazinocarbonyl-phenyl)-trimethyl-ammonium iodide in 9 mL of ethanol 0.245 mL of salicylaldehyde is added dropwise at room temperature. After addition of 0.5 mL of concentrated hydrochloric acid stirring is continued for 16 hours at room temperature. A colorless precipitate is then filtrated off and dried in the vacuum at 30° C. This iodide salt was solved in water and passed over a DOWEX 1×8 packed column. The combined water eluates were evaporated in vacuum to obtain a beige solid in 20% yield.

APPLICATION EXAMPLES

Application Example 1

Peroxide Bleaching of Morin in Solution 2.5 µM catalyst solution (1:1 complex of Mn(II) chloride tetrahydrate with the ligand in question in water or methanol) are added at time t=0 to a solution of 160 µM morin in 10 mM carbonate buffer, pH 10 containing 10 mmol/l hydrogen peroxide. The solution is located in a thermostatically controllable vessel, equipped with a magnetic stirrer, at 23° C. The extinction of the solution is measured at 410 nm over a period of 10 min. The values for the decoloration after 3 min. are indicated as percentages.

The following ligands were used:

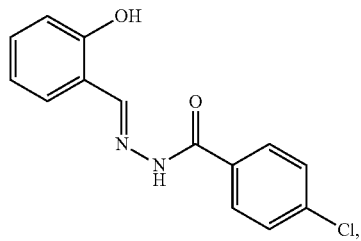
L1

E/Z-isomers and tautomeric forms

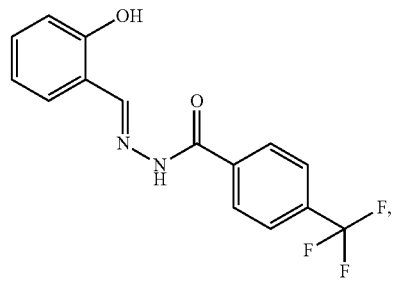
L7

E/Z-isomers and tautomeric forms

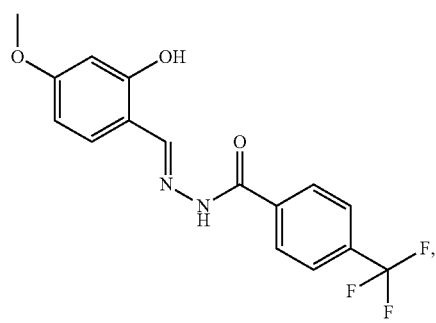
L8

E/Z-isomers and tautomeric forms

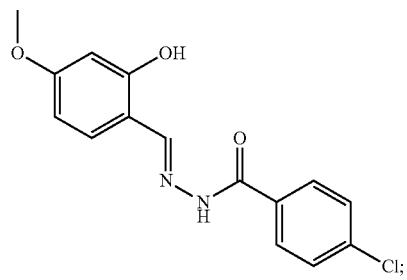
L3

E/Z-isomers and tautomeric forms

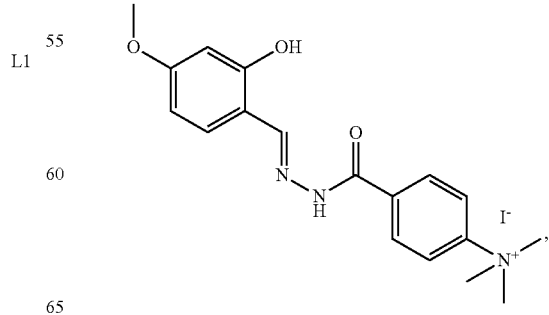
L9

E/Z-isomers and tautomeric forms

-continued

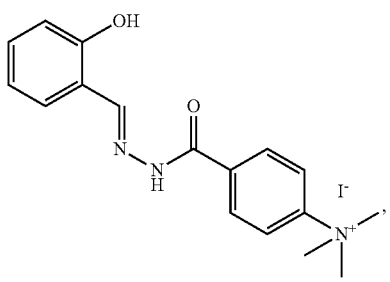

E/Z-isomers and tautomeric forms

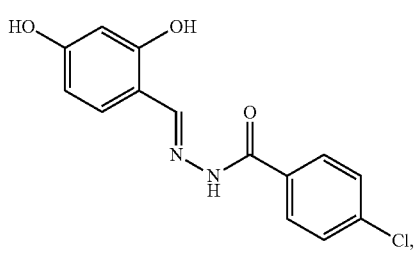

E/Z-isomers and tautomeric forms

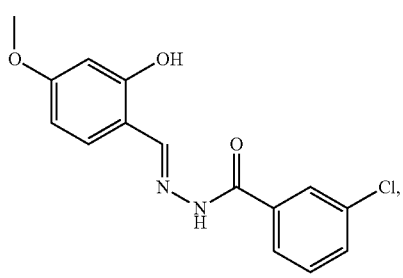

E/Z-isomers and tautomeric forms

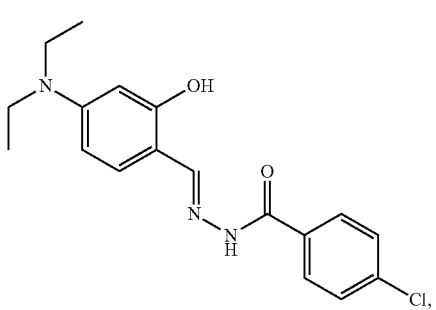

E/Z-isomers and tautomeric forms

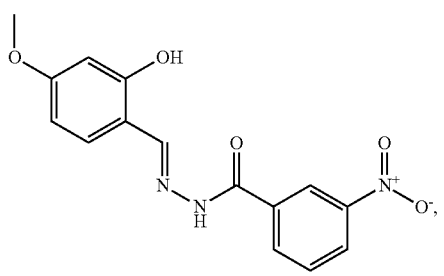

E/Z-isomers and tautomeric forms

-continued

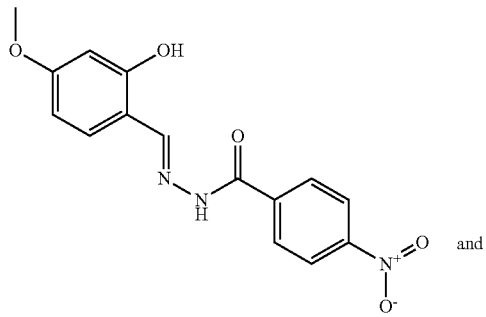

and

E/Z-isomers and tautomeric forms

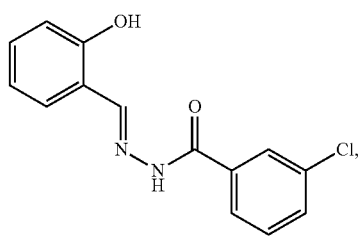

E/Z-isomers and tautomeric forms

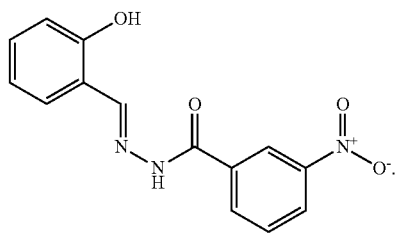

E/Z-isomers and tautomeric forms

TABLE 1

| Ligand | Extent of the decoloration after 3 min (%) |
|---|---|
| L10 | 80 |
| L9 | 85 |
| L8 | 77 |
| L1 | 81 |
| L7 | 85 |
| L3 | 80 |
| L4 | 46 |
| L6 | 84 |
| L5 | 29 |
| L11 | 82 |
| L13 | 83 |
| L2 | 84 |
| Reference without catalyst | 3 |

The bleaching action of the compounds according to the invention is by far superior to the reference of 10 mM hydrogen peroxide alone.

Application Example 2

Peroxide Bleaching Action in Washing Agents 7.5 g of white cotton fabric and 2.5 g of tea-stained cotton fabric are treated in 80 ml of washing liquor. The liquor contains a standard washing agent (ECE, 456 IEC) in a concentration of 7.5 g/l. The hydrogen peroxide concentration is 8.6 mmol/l. The catalyst concentration (1:1 complex of manganese(II) chloride tetrahydrate with the ligand in question, prepared in methanolic solution with the addition of a small amount of lithium hydroxide) is 50 μmol/l. The washing process is carried out in a steel beaker in a LINITEST apparatus for 30 minutes at 40° C. For evaluating the bleaching results, the increase in the lightness DY (difference in lightness according to CIE) of the stains brought about by the treatment is determined spectrophotometrically in difference to values obtained without the addition of a catalyst. A value >0 indicates catalytic activity.

TABLE 2

| 1:1 Mn complex with ligand | DY increase on top of peroxide |
|---|---|
| L10 | 5.6 |
| L9 | 6.0 |
| L8 | 5.9 |
| L1 | 5.2 |
| L7 | 2.3 |
| L3 | 3.9 |
| L4 | 3.2 |
| L13 | 4 |
| L6 | 5.9 |
| L5 | 3.8 |
| L11 | 3.6 |
| L1 | 3.7 |
| L12 | 3 |

As can be seen from Table 2 above, the manganese complexes exhibit a very good bleaching action.

The results of Table 2 show, that those manganese complexes with ligands bearing an electron attracting group exhibit enhanced bleaching performance.

Application Example 3

With Un-Complexed Liqands: (Peroxide Bleaching Action in Washing Agents)

22.4 g of white cotton fabric and 0.8 g of BC01 tea-stained or EMPA114 red wine-stained cotton fabric are treated in 150 ml of washing liquor. The liquor contains a commercial color care washing powder in a concentration of 4.5 g/l, and 0.83 g/l sodium percarbonate (SPC). The catalyst concentration ligand L10 in an un-complexed form is 20 μmol/l. The washing process is carried out in a steel beaker in a LINITEST apparatus for 40 minutes at 30° C. For evaluating the bleaching results, the increase in the lightness DY (difference in lightness according to CIE) of the stains brought about by the treatment is determined spectrophotometrically. The higher the ΔY value, the better the bleach performance

TABLE 3

| ΔY of Acylhydrazone Ligand with SPC containing detergent | | |
|---|---|---|
| | BC01 | EMPA114 |
| Percarbonate alone | 6.2 | 21.0 |
| Percarbonate + L10 | 10.4 | 26.8 |

As can be seen from Table 3 above, the Ligand L10 alone exhibits a very good bleaching action.

Application Example 4

With Un-Complexed Liqands: (Bleach Activity on Top of TAED Action in Washing Agents)

22.4 g of white cotton fabric and 0.8 g of BC01 tea-stained or EMPA114 red wine-stained cotton fabric are treated in 150 ml of washing liquor. The liquor contains a commercial color care washing powder in a concentration of 4.5 g/l, 0.83 g/l sodium percarbonate (SPC) and 0.166 g Tetraacetyethylenediamin (TAED). The catalyst concentration Ligand L10 in a un-complexed form is 20 μmol/l. The washing process is carried out in a steel beaker in a LINITEST apparatus for 40 minutes at 30° C. For evaluating the bleaching results, the increase in the lightness DY (difference in lightness according to CIE) of the stains brought about by the treatment is determined spectrophotometrically. The higher the ΔY value, the better the bleach performance

TABLE 4

| ΔY of Acylhydrazone Ligand with SPC/TAED containing detergent | | |
|---|---|---|
| | BC01 | EMPA114 |
| SPC/TAED | 9.1 | 24.9 |
| SPC/TAED + L10 | 15.1 | 30.0 |

As can be seen from Table 4 above, the Ligand L10 exhibits a very good bleaching action, even on top of a SPC/TAED bleach system.

Application Example 5

Un-Complexed Ligand: (Bleach Activity with AATCC Standard Detergent)

22.4 g of white cotton fabric and 0.8 g of BC01 tea-stained cotton fabric are treated in 150 ml of washing liquor. The liquor contains AATCC standard powder detergent in a concentration of 7.5 g/l, 0.68 g/l sodium percarbonate (SPC) and 0.151 g Tetraacetyethylenediamin (TAED). The catalyst concentration Ligand L9 in a un-complexed form is 20 μmol/l. The washing process is carried out in a steel beaker in a LINITEST apparatus for 40 minutes at 40° C. For evaluating the bleaching results, the increase in the lightness DY (difference in lightness according to CIE) of the stains brought about by the treatment is determined spectrophotometrically. The higher the ΔY value, the better the bleach performance

TABLE 5

| ΔY of Acylhydrazone Ligand with AATCC detergent | |
|---|---|
| | BC01 |
| SPC/TAED | 12.7 |
| SPC + L9 | 14.8 |

As can be seen from Table 5 above, the ligand L9 exhibits a very good bleaching action, which exceeds the performance of the standard bleach system SPC/TAED.

Application Example 6

Un-Complexed Ligand: (Bleach Activity with Liquid Bleach Additive)

48 g of white cotton fabric and 0.8 g of BC01 tea-stained and 0.8 g EMPA114 red wine or 0.8 g BC03 tea and BC06 strawberry-stained cotton fabric are treated in 250 ml of washing liquor. The liquor contains a commercial color care washing powder in a concentration of 4.5 g/l, 2.4 g/l of a commercial liquid bleach additive (Vanish). The catalyst concentration Ligand L10 in a un-complexed form is 10 μmol/l and 20 μmol/l. The washing process is carried out in a steel beaker in a LINITEST apparatus for 40 minutes at 40° C. For evaluating the bleaching results, the increase in the lightness DY (difference in lightness according to CIE) of the stains brought about by the treatment is determined spectrophotometrically. The higher the ΔY value, the better the bleach performance.

TABLE 6

Acylhydrazone ligand with detergent and bleach additive

|  | BC01 | EMPA114 | BC03 | BC06 |
|---|---|---|---|---|
| Detergent | 2.7 | 16.3 | 1.9 | 0.1 |
| Detergent + Bleach additive | 6.2 | 22.4 | 5.1 | 4.9 |
| Detergent + Bleach additive + 10 μmol/l L10 | 8.1 | 23.2 | 8.4 | 5.9 |
| Detergent + Bleach additive + 20 μmol/l L10 | 10.4 | 26.7 | 12.8 | 8.7 |

As can be seen from Table 6 above, the ligand L10 exhibits a very good bleaching action also with liquid bleach additives.

Application Example 7

Un-Complexed Ligand: (Incorporation of L10 into Liquid Bleach Additive)

3.02 mmol/l of L10 (counter ion Cl⁻) are incorporated into a commercial liquid bleach additive. This additive is applied in a bleach experiment immediately, 1 day, one week and one month after preparation, storage of the bleach additive at ambient temperature.

The washing process is as follows:

24.2 g of white cotton fabric and 0.8 g of BC01 tea-stained cotton fabric are treated in 150 ml of washing liquor. The liquor contains a commercial color care washing powder in a concentration of 4.5 g/l, 3.7 g/l of the commercial liquid bleach additive containing the catalyst concentration Ligand L10 (counter ion Cl⁻) in a un-complexed form. The washing process is carried out in a steel beaker in a LINITEST apparatus for 40 minutes at 40° C. For evaluating the bleaching results, the increase in the lightness DY (difference in lightness according to CIE) of the stains brought about by the treatment is determined spectrophotometrically. The higher the ΔY value, the better the bleach performance.

TABLE 7

L10 containing liq. bleach additive, performance after storage (ΔY BC01)

|  | immediately | 1 day | 1 week | 1 month |
|---|---|---|---|---|
| L10-Bleach additive | 10.4 | 10.4 | 10.8 | 10.1 |

The application of the bleach additive without L10 leads to a ΔY of 6.5

The results in Table 7 indicate no loss in bleach activity after a storage time of one month.

Additionally the content of hydrogen peroxide in the bleach additive is determined iodometrically

TABLE 8 concentration of hydrogen peroxide (mol/l) in L10 containing bleach additive after storage

|  | immediately | 1 day | 1 week | 1 month |
|---|---|---|---|---|
| L10 Bleach additive | 1.93 | 1.93 | 1.92 | 1.92 |

Table 8 indicates that no peroxide is decomposed in the presence of L10.

Application Example 8

Un-Complexed Ligand: (Dishwashing)

Tee-stained cups are prepared according to the IKW method ("IKW-Arbeitskreis Maschinenspülmittel, Methoden zur Bestimmung der Reinigungsleistung von maschinellen Geschirrspülmitteln (Part A and B)", SÖFW, 11+14, 1998). Tea-stained cups are filled with a carbonate buffer solution (pH 9.6) containing 44 mM hydrogen peroxide and 30 μM catalyst. After 15 minutes the solution is removed, and the cups are rinsed with water. The removal of the tea deposit is evaluated visually on a scale from 0 (i.e. unchanged, very strong deposit) to 10 (i.e. no deposit). A rating of 4.5 is observed in experiments without catalyst.

TABLE 9

| Catalyst (Ligand) | Rating |
|---|---|
| Reference | 4.5 |
| Ligand 10 | 8 |
| Ligand 121 of Synthesis Example 21 | 7 |

The invention claimed is:

1. A compound of formula (5)

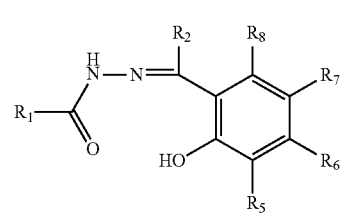

(5)

wherein $R_1$ is phenyl substituted with 1 to 5 electron withdrawing substituents —$N(R_{100}R'_{100}R''_{100})_3{}^+A^-$, wherein $R_{100}$, $R'_{100}$ and $R''_{100}$ independently are hydrogen, $C_1$-$C_{18}$alkyl or phenyl or two of $R_{100}$, $R'_{100}$ and $R''_{100}$ together with the nitrogen atom to which they are bonded form a 5 or 6 membered-ring which may contain a further nitrogen atom and $A^-$ is an anion or $R_1$ together with the electron withdrawing substituent is a group

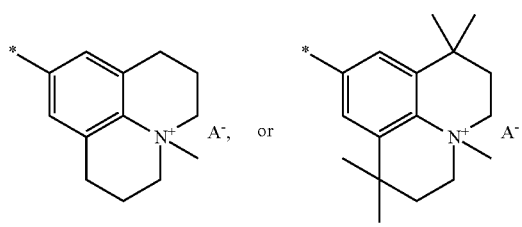

where * is the point of attachment;

$R_2$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted aryl or unsubstituted or substituted heteroaryl; and $R_5$, $R_6$, $R_7$ and $R_8$ independently from each other are hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, —$OR_{100}$, —$NR_{100}R'_{100}$, halogen or a group

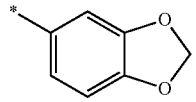 [SMILES: *c1ccc2c(c1)OCO2]

or independently have the meaning as defined for $R_1$ or $R_5$ and $R_6$, $R_6$ and $R_7$ or $R_7$ and $R_8$ are linked together to form 1, 2, 3 or 4 carbocyclic or heterocyclic rings which may be uninterrupted or interrupted by one or more —O—, —S— or —$NR_9$— and/or which may be further fused with other aromatic rings and/or which may be substituted with one or more $C_1$-$C_6$alkyl groups.

* * * * *